(12) United States Patent
Hsia

(10) Patent No.: US 11,206,861 B2
(45) Date of Patent: *Dec. 28, 2021

(54) COMPOSITIONS AND METHODS FOR ENHANCING CANCER RADIOTHERAPY

(71) Applicant: Houn Simon Hsia, Irvine, CA (US)

(72) Inventor: Houn Simon Hsia, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/338,678

(22) PCT Filed: Oct. 3, 2017

(86) PCT No.: PCT/US2017/054988
§ 371 (c)(1),
(2) Date: Apr. 1, 2019

(87) PCT Pub. No.: WO2018/067604
PCT Pub. Date: Apr. 12, 2018

(65) Prior Publication Data
US 2020/0260772 A1    Aug. 20, 2020

Related U.S. Application Data

(60) Provisional application No. 62/403,630, filed on Oct. 3, 2016.

(51) Int. Cl.
*A61P 35/04*     (2006.01)
*A23L 33/00*     (2016.01)
*A61K 45/06*     (2006.01)

(52) U.S. Cl.
CPC .............. *A23L 33/40* (2016.08); *A61P 35/04* (2018.01); *A61K 45/06* (2013.01)

(58) Field of Classification Search
CPC ................................ A23L 33/40; A61P 35/04
See application file for complete search history.

(56) References Cited

U.S. PATENT DOCUMENTS

| | | | |
|---|---|---|---|
| 4,348,483 A | 9/1982 | Skogerson |
| 4,569,836 A | 2/1986 | Gordon |
| 5,810,888 A | 9/1998 | Fenn |
| 5,976,548 A | 11/1999 | Hsia et al. |
| 6,197,295 B1 | 3/2001 | Hsia et al. |
| 6,440,464 B1 | 8/2002 | Hsia et al. |
| 7,906,554 B2 | 3/2011 | Kelly |
| 8,017,147 B2 | 9/2011 | Mazed et al. |
| 8,257,694 B2 | 9/2012 | Daikeler et al. |
| 8,343,843 B2 | 1/2013 | Lee |
| 9,072,768 B2 | 7/2015 | Ranganathan |
| 9,095,602 B2 | 8/2015 | Gleave et al. |
| 9,889,092 B2 | 2/2018 | Corbin |
| 2004/0072775 A1 | 4/2004 | Sobol et al. |
| 2004/0087490 A1 | 5/2004 | Troup et al. |
| 2005/0013875 A1 | 1/2005 | Kobayashi et al. |
| 2006/0275506 A1 | 12/2006 | Fisher et al. |
| 2009/0110674 A1 | 4/2009 | Loizou |
| 2011/0008457 A1 | 1/2011 | Newman et al. |
| 2011/0189220 A1 | 8/2011 | Yang et al. |
| 2011/0229447 A1 | 9/2011 | Schiffrin et al. |
| 2012/0010688 A1 | 1/2012 | Lamb |
| 2014/0294795 A1 | 10/2014 | Hsia |
| 2015/0004130 A1 | 1/2015 | Faber et al. |
| 2015/0164964 A1 | 6/2015 | El-Nezamy et al. |
| 2016/0067202 A1 | 3/2016 | Mathisen |
| 2016/0354344 A1 | 12/2016 | Robertson et al. |
| 2017/0246136 A1 | 8/2017 | Pena Diaz et al. |
| 2018/0037263 A1 | 2/2018 | Kanasugi |

FOREIGN PATENT DOCUMENTS

| | | |
|---|---|---|
| CN | 105641000 A | 6/2016 |
| EP | 0385859 A1 | 9/1990 |
| WO | WO-0007607 A1 | 2/2000 |
| WO | WO-02076548 A2 | 10/2002 |
| WO | WO-2011115062 A1 | 9/2011 |
| WO | WO-2012122295 A2 | 9/2012 |
| WO | WO-2014054884 A1 | 4/2014 |
| WO | WO-2015013932 A1 | 2/2015 |
| WO | WO-2018231937 A2 | 12/2018 |
| WO | WO-2018231943 A2 | 12/2018 |

OTHER PUBLICATIONS

Extended European Search Report for Application No. EP17859044. 4, dated Oct. 2, 2019, 10 pages.
Benswell Corporation Ltd, Prowell Nutritions "Good Health—Good Life" by Nutrawell, 2015, 18 pages, Retrieved from the Internet [URL: http://www.prowellnutritions.com].
Turk H.F., "Alteration of EGFR Spatiotemporal Dynamics Suppresses Signal Transduction," PloS One, 2012, vol. 7 (6), e39682, pp. 1-18.
Co-pending U.S. Appl. No. 12/833,207, filed Jul. 9, 2010, 33 pages.
Daenen L.G., et al., "Increased Plasma Levels of Chemoresistance-inducing Fatty Acid 16:4(N-3) After Consumption of Fish and Fish Oil," JAMA Oncology, 2015, vol. 1 (3), pp. 350-358.
Durrani F., et al., "Synergistic Effect of Selenium Compounds with Radiation Therapy in Human A549 Lung Xenografts," Cancer Research, 2007, vol. 67 (9), 4 pages.
Fahmy et al., "Protective Effects of Omega-3 Fatty Acids and/ or Nano-selenium on Cisplatin and Ionizing Radiation Induced Liver Toxicity in Rats," Indian Journal of Pharmaceutical Education and Research, 2016, vol. 50 (4), pp. 649-656.
Lockwood K., et al., "Apparent Partial Remission of Breast Cancer in 'High Risk' Patients Supplemented with Nutritional Antioxidants, Essential Fatty Acids, and Coenzymes Q10," Molecular Aspects of Medicine, 1994, vol. 15 (Supplemental), pp. S231-S240.

(Continued)

*Primary Examiner* — Heidi Reese
(74) *Attorney, Agent, or Firm* — Fish IP Law, LLP

(57) ABSTRACT

A nutritional supplement is described that enhances and provides synergistic effects when used in combination with radiotherapy to treat tumors, both reducing tumor size and preventing metastasis. The nutritional supplement has been also found to be effective in reducing negative side effects of concurrent radiotherapy, including inflammation, weight loss, muscle wasting, neutropenia, and loss of cells from the lining of the gut.

16 Claims, 52 Drawing Sheets

(56) References Cited

OTHER PUBLICATIONS

Luo H., et al., "Selenium Nanoparticles Inhibit the growth of Hela and MDA-MB-231 Cells Through Induction of S Phase Arrest," Colloids and Surfaces B: Biointerfaces, 2014, vol. 94, pp. 304-308.
Simone C., et al., "Antioxidants and Other Nutrients Do Not Interfere with Chemotherapy or Radiation Therapy and Can Increase Kill and Increase Survival, Part 2," Alternative Therapies in Health and Medicine, 2007, vol. 13 (2), pp. 40-47.
Wang H., et al., "Reduction of Splenic Immunosuppressive Cells and Enhancement of Anti-tumor Immunity by Synergy of Fish Oil and Selenium Yeast," PloS One, 2013, vol. 8 (1), e52912, pp. 1-11.
Norman H. A., "The Role of Dietary Supplements During Cancer Therapy," The Journal of Nutrition, 2003, vol. 133 (11), pp. 3794S-3799S.
Yang Y.S., et al., "Enhancing Radiotherapy by Lipid Nanocapsule-mediated Delivery of Amphiphilic Gold Nanoparticles to Intracellular Membranes," ACS Nano, Sep. 2014, vol. 8 (9), pp. 8992-9002.
Co-pending U.S. Appl. No. 60/290,861, filed May 14, 2001.
Gandhi U.H., et al., "Selenium Suppresses Leukemia Through the Action of Endogenous Eicosanoids," Cancer Research, 2014, vol. 74 (14), pp. OF1-OF12.

Hwang J.T., et al., "Selenium Regulates Cyclooxygenase-2 and Extracellular Signal-Regulated Kinase Signalling Pathways by Activating AMP-Activated Protein Kinase in Colon Cancer Cells," Cancer Research, 2006, vol. 66 (20), pp. 10057-10063.
International Search Report and Written Opinion for Application No. PCT/US2017/054988, dated Jan. 15, 2018, 12 pages.
International Search Report and Written Opinion for Application No. PCT/US2018/037263, dated Feb. 15, 2019, 16 pages.
International Search Report and Written Opinion for Application No. PCT/US2018/037268, dated Nov. 13, 2018, 14 pages.
International Search Report and Written Opinion for Application No. PCT/US2018/037274, dated Jan. 25, 2019, 25 pages.
Ma H., et al., "Efficacy of Dietary Antioxidants Combined with A Chemotherapeutic Agent on Human Colon Cancer Progression in a Fluorescent Orthotopic Mouse Model", Anticancer Research, 2009, vol. 29, pp. 2421-2426.
Xu et al., Colloids and Surfaces B: Biointerfaces, 2006, vol. 48 (1), pp. 50-57.
Choy and Milas, Journal of the National Cancer Institute (2003), vol. 95 (19), pp. 1140-1452.
Lederer S., et al., "Additive Dose Response Models: Explicit Formulation and the Loewe Additivity Consistency Condition", Frontiers in Pharmacology, Feb. 2018, vol. 9 (31), 11 pages.

|     | Bax | Bcl-2 | Bax/Bcl-2 | caspase 3 |
| --- | --- | --- | --- | --- |
| T   | 0.31±0.00 | 1.41±0.67 | 0.22±0.12 | 1.03±0.88 |
| TN  | 5199.29±2321.78 | 241.89±7.44 | 21.49±10.19 | 47708.35±7808.87 |
| TR  | 1.09±1.39 | 0.99±0.16 | 1.10±0.03 | 0.71±0.06 |
| TRN | 7858.24±1593.75 | 213.40±8.45 | 36.82±9.56 | 46977.1±5263.41 |

FIG. 14

COMPOSITIONS AND METHODS FOR ENHANCING CANCER RADIOTHERAPY

This application claims priority to U.S. Provisional Application No. 62/403,630 filed on Oct. 3, 2016 and U.S. Provisional Application No. 62/519,087, filed Jun. 13, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is cancer radiotherapy.

BACKGROUND

The following description includes information that may be useful in understanding the present invention. It is not an admission that any of the information provided herein is prior art or relevant to the presently claimed invention, or that any publication specifically or implicitly referenced is prior art.

Radiotherapy and chemotherapy protocols utilized in the treatment of cancer can clearly benefit patients, but can be ineffective or less effective with some cancers. In addition both radiotherapy and chemotherapy are associated with significant side effects, including nausea, weight loss, hair loss, damage to the gastrointestinal tract, and skin irritation.

Attempts have been made to enhance the effectiveness of radiotherapy. For example, gold nanoparticles that have been modified to target tumor cells have been used to enhance radiotherapy (Yang et al, ACS Nano, 2014, 8(9): 8992-9002). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Similarly, COX-2 inhibitors have been used to selectively sensitize tumor cells to the effects of radiation (Choy and Milas, J. Natl Cancer Inst (2003) 95(19):1140-1452). Such approaches, however, can have issues with selectivity and may not be effective against all tumor types. To date attempts to reduce the side effects of radiotherapy are primarily directed to partitioning the total radiation dose into a number of smaller radiation doses (leaving time in between to allow for recovery), targeting of tumor using shielding, and identification of the boundaries of the tumor and localization of radiotherapy to that site. Unfortunately, such approaches can fail to adequately treat all of the tumor cells.

Attempts have also been made to enhance the effects of chemotherapy. Some studies have suggested that consumption of fish oil can improve results from chemotherapy, however other research has suggested that fish oil can interfere (Daenen et al, JAMA Oncol (2015) 1(3):350-358). Formulation of chemotherapeutic agents as nanoparticles has also been attempted (Xu et al, Coll. Surf. B: Biointerfaces (2006) 48(1):50-57). It is unclear, however, if all chemotherapeutic drugs are suitable for such reformulation. Codelivery of chemotherapeutic drugs with siRNA designed to interfere with multi-drug resistance has also been explored. Such siRNAs, however, are sequence specific and may not be suitable for some tumors.

Mitigation of the side effects of chemotherapy are generally directed at providing symptomatic relief. For example, antiemetics can be used to reduce nausea, along with diet modification and eating small, frequent meals that avoid certain foods. Unfortunately such approaches are not always effective. In some instances chemotherapeutic agents are selected to have reduced toxicity in order to reduce side effects, however such agents may also have reduced effectiveness against tumor cells.

Thus, there is still a need for safe and effective compositions and methods to enhance the effectiveness and/or reduce the side effects of cancer radiotherapy.

SUMMARY OF THE INVENTION

The inventive subject matter provides apparatus, systems and methods in which a nutritional supplement as shown in Table 1 is used in combination with radiotherapy to treat a tumor and/or reduce or eliminate negative side effects of cancer radiotherapy.

One embodiment of the inventive concept is a method of treating a tumor that includes applying a radiotherapy protocol to a patient in need of treatment and providing the patient with a nutritional supplement formulated as listed in Table 1, where the nutritional supplement is provided in an amount that provides a synergistic effect in reducing tumor volume or weight. In some embodiments the method of claim 1, wherein the nutritional supplement is provided to the patient prior to the initiation of radiotherapy.

Another embodiment of the inventive concept is a method of reducing side effects of radiotherapy that includes applying a radiotherapy protocol to a patient in need of treatment and providing the patient with a nutritional supplement formulated as shown in Table 1, in an amount that is effective to reduce a side effect of the radiotherapy protocol. In some embodiments the nutritional supplement is provided to the patient prior to the initiation of radiotherapy.

Another embodiment of the inventive concept is a method of modulating gene expression in a tumor by providing a nutritional supplement formulated as shown in Table 1 to a tumor or an animal having a tumor, where the nutritional supplement comprises a plurality of components as and is provided in an amount sufficient to modulate expression of a gene of the tumor. The nutritional supplement can be provided prior to the initiation of a radiotherapy protocol and/or during the application of radiotherapy. In some embodiments the gene encodes for an angiogenesis factor. In other embodiments the gene encodes for an apoptosis factor.

Another embodiment of the inventive concept is a method of reducing metastasis from a tumor by providing a patient having a metastatic tumor with a nutritional supplement formulated as in Table 1, where the nutritional supplement is provided in an amount to reduce metastatic activity of the tumor. The nutritional supplement can be provided prior to and/or concurrently with radiotherapy.

Another embodiment of the inventive concept is a method of reducing angiogenesis in a tumor by providing a patient having a tumor with a nutritional supplement formulated as shown in Table 1, where the nutritional supplement is provided in an amount to reduce an angiogenic activity of the tumor. The nutritional supplement can be provided prior to or concurrently with radiotherapy.

Another embodiment of the inventive concept is a method of reducing growth of a cancer stem cell by providing a patient having a tumor that includes the cancer stem cell with a nutritional supplement formulated as in Table 1, where the nutritional supplement is provided in an amount to reduce growth of the cancer stem cell. The nutritional supplement can be provided prior to or concurrently with radiotherapy.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 depicts a typical treatment protocol, where nutritional supplementation is provided starting either 7 days prior to implementation of radiotherapy or simultaneously with tumor cell implantation. In this study mice were sacrificed 21 days after tumor cell implantation.

FIG. 2A shows changes in body weight observed during a treatment protocol as in FIG. 1. FIG. 2B provides a histogram of results from a similar study.

FIGS. 3A to 3D show synergistic effects observed on tumor volume and weight in mice treated with radiotherapy and a nutritional supplement of the inventive concept. FIG. 3A shows tumor volume over 21 days. FIG. 3B shows tumor volume on days 7 to 11. FIG. 3C shows tumor weight following different treatment regimes. Statistically significant differences are indicated (* to ***). FIG. 3D provides photographs of tumors excised from mice following treatment with different regimes.

FIGS. 4A to 4E show the degree of common radiotherapy side effects related to muscle mass and organ weight in mice treated with radiotherapy alone, a nutritional supplement of the inventive concept, and combined therapy. Statistically significant differences are indicated (* to ***). FIG. 4A shows the effect of treatment using radiotherapy, a nutritional supplement of the inventive concept, and combined treatment on gastrocnemius muscle mass 21 days after tumor cell injection. FIG. 4B shows the effect of treatment using radiotherapy, a nutritional supplement of the inventive concept, and combined treatment on soleus muscle mass 21 days after tumor cell injection. FIG. 4C shows the effect of treatment using radiotherapy, a nutritional supplement of the inventive concept, and combined treatment on lung (inclusive of metastatic tumor) weight 21 days after tumor cell injection. FIG. 4D shows the effect of treatment using radiotherapy, a nutritional supplement of the inventive concept, and combined treatment on liver (inclusive of metastatic tumor) weight 21 days after tumor cell injection. FIG. 4E shows the effect of treatment using radiotherapy, a nutritional supplement of the inventive concept, and combined treatment on spleen (inclusive of metastatic tumor) weight 21 days after tumor cell injection.

FIGS. 5A to 5G show the degree of common radiotherapy side effects related to various blood cell populations in mice treated with radiotherapy alone, a nutritional supplement of the inventive concept, and combined therapy. Statistically significant differences are indicated (* to ***). FIG. 5A shows the effect of treatment using radiotherapy, a nutritional supplement of the inventive concept, and combined treatment on red blood cell count 21 days after tumor cell injection. FIG. 5B shows the effect of treatment using radiotherapy, a nutritional supplement of the inventive concept, and combined treatment on granulocyte count 21 days after tumor cell injection. FIG. 5C shows the effect of treatment using radiotherapy, a nutritional supplement of the inventive concept, and combined treatment on platelet count 21 days after tumor cell injection. FIG. 5D shows the effect of treatment using radiotherapy, a nutritional supplement of the inventive concept, and combined treatment on white blood cell count 21 days after tumor cell injection. FIG. 5E shows the effect of treatment using radiotherapy, a nutritional supplement of the inventive concept, and combined treatment on lymphocyte count 21 days after tumor cell injection. FIG. 5F shows the effect of treatment using radiotherapy, a nutritional supplement of the inventive concept, and combined treatment on granulocyte count 21 days after tumor cell injection. FIG. 5G shows the effect of treatment using radiotherapy, a nutritional supplement of the inventive concept, and combined treatment on neutrophil/lymphocyte percentage ratio 21 days after tumor cell injection.

FIGS. 6A to 6G show the degree of common radiotherapy side effects related to serum biochemistry, kidney function, and liver function in mice treated with radiotherapy alone or radiotherapy, a nutritional supplement of the inventive concept, and combined therapy. Statistically significant differences are indicated (* to ***). FIG. 6A shows the effect of treatment using radiotherapy, a nutritional supplement of the inventive concept, and combined treatment on serum albumin 21 days after tumor cell injection. FIG. 6B shows the effect of treatment using radiotherapy, a nutritional supplement of the inventive concept, and combined treatment on serum creatinine 21 days after tumor cell injection. FIG. 6C shows the effect of treatment using radiotherapy, a nutritional supplement of the inventive concept, and combined treatment on blood urea nitrogen 21 days after tumor cell injection. FIG. 6D shows the effect of treatment using radiotherapy, a nutritional supplement of the inventive concept, and combined treatment on total bilirubin 21 days after tumor cell injection. FIG. 6E shows the effect of treatment using radiotherapy, a nutritional supplement of the inventive concept, and combined treatment on serum glutamic oxaloacetic transaminase 21 days after tumor cell injection. FIG. 6F shows the effect of treatment using radiotherapy, a nutritional supplement of the inventive concept, and combined treatment on serum glutamic-pyruvic transaminase 21 days after tumor cell injection. FIG. 6G shows the effect of treatment using radiotherapy, a nutritional supplement of the inventive concept, and combined treatment on serum glucose 21 days after tumor cell injection.

FIGS. 7A and 7B show the effect of treatment with a nutritional supplement of the inventive concept on inflammation that is associated with tumor growth and with radiotherapy. Mice were treated with radiotherapy alone, a nutritional supplement of the inventive concept, or combined therapy. Statistically significant differences are indicated (* to ***). FIG. 7A shows the effect of treatment using radiotherapy, a nutritional supplement of the inventive concept, and combined treatment on serum IL-6 21 days after tumor cell injection.

FIG. 7B: shows the effect of treatment using radiotherapy, a nutritional supplement of the inventive concept, and combined treatment on serum IL-1β 21 days after tumor cell injection.

FIGS. 8A to 8G show the effect of treatment with a nutritional supplement of the inventive concept on gene expression in tissue and in tumor cells. Mice were treated with radiotherapy alone, a nutritional supplement of the inventive concept, or combined therapy. Statistically significant differences are indicated (* to ***). FIG. 8A shows the effect of treatment using radiotherapy, a nutritional supplement of the inventive concept, and combined treatment on expression of the VEGF gene in an implanted tumor 21 days after tumor cell injection. FIG. 8B shows the effect of treatment using radiotherapy, a nutritional supplement of the inventive concept, and combined treatment on expression of the BAX gene in an implanted tumor 21 days after tumor cell injection. FIG. 8C shows the effect of treatment using radiotherapy, a nutritional supplement of the inventive concept, and combined treatment on expression of the Bcl-2 gene in an implanted tumor 21 days after tumor cell injection. FIG. 8D shows the effect of treatment using radiotherapy, a nutritional supplement of the inventive concept, and combined treatment on expression of the caspase 3 gene in an implanted tumor 21 days after tumor cell injection. FIG. 8E shows the effect of treatment using radiotherapy, a nutritional supplement of the inventive concept, and combined treatment on expression of the BAX gene in lung 21 days after tumor cell injection. FIG. 8F shows the effect of treatment using radiotherapy, a nutritional supplement of the inventive concept, and combined treatment on expression of the Bcl-2 gene in lung 21 days after tumor cell injection. FIG. 8G shows the effect of treatment using radiotherapy, a nutritional supplement of the inventive concept, and combined treatment on expression of the caspase 3 gene in lung 21 days after tumor cell injection.

FIG. 9 depicts an alternative treatment/study protocol. FIG. 9 depicts a treatment/study protocol in which mice receive radiotherapy on days 8, 10, and 12, with nutritional supplementation beginning with the initiation of radiotherapy. Mice are sacrificed at day 14 or at day 24 following implantation of tumor cells.

FIGS. 10A to 10C show results of serum albumin and blood cell population studies performed on mice treated with the protocol shown in FIG. 9. Statistically significant differences are indicated (* to ***). FIG. 10A shows serum albumin concentration at 14 days and 24 days following tumor cell implantation in mice treated as shown in FIG. 9. FIG. 10B shows lymphocyte counts at 14 days and 24 days following tumor cell implantation in mice treated as shown in FIG. 9. FIG. 10C shows N/L Ratios at 14 days and 24 days following tumor cell implantation in mice treated as shown in FIG. 9.

FIGS. 11A to 11D show results of studies of expression of tumor markers and studies of tumor metastatis performed on mice treated with the protocol shown in FIG. 9. FIG. 11A shows the results of immunofluorescence studies of VEGF expression within a tumor mass 24 days following tumor cell implantation in mice treated as shown in FIG. 9. FITC represents VEGF-specific staining. FIG. 11B shows the results of immunofluorescence studies of VEGF expression within the lung (metastasis) 24 days following tumor cell implantation in mice treated as shown in FIG. 9. FITC represents VEGF-specific staining. FIG. 11D shows the results of immunofluorescence studies of EGFR expression within the tumor mass 24 days following tumor cell implantation in mice treated as shown in FIG. 9. FITC represents EGFR-specific staining in mice treated as shown in FIG. 9. FITC represents CD31-specific staining.

FIG. 12 shows results of studies of cancer stem cell distribution performed on mice treated with the protocol shown in FIG. 9. Immunofluorescence was used to visualize CD31 (a cancer stem cell marker) expression within the tumor mass and in lung tissue (metastasis) 24 days following tumor cell implantation.

FIG. 13 shows results of studies of the degree of hypoxia in primary and metastatic tumor sites performed on mice treated with the protocol shown in FIG. 9. Immunofluorescence was used to visualize H1F1-α (a hypoxia marker) expression within the tumor mass and in lung tissue (metastasis) 24 days following tumor cell implantation in mice treated as shown in FIG. 9. FITC represents H1F1-α-specific staining.

FIG. 14: FIG. 14 shows results of qPCR studies of apoptosis marker expression in tumors, performed on mice treated with the protocol shown in FIG. 9. Studies were performed 24 days after tumor cell implantation.

FIG. 15 depicts an alternative treatment/study protocol. FIG. 15 depicts a treatment/study protocol in which mice receive radiotherapy on days 8, 10, and 12, with nutritional supplementation provided prior to tumor cell implantation, at the time of tumor cell implantation, or at the initiation of radiotherapy. Mice are sacrificed at day 21 following implantation of tumor cells.

FIG. 16 shows photomicrographs of gut cellular architecture in mice treated with the protocol shown in FIG. 15.

FIGS. 17A to 17F depicts results from studies of gene expression in tumor cells of mice treated with the protocol shown in FIG. 15. Statistically significant differences are indicated (* to ***). FIG. 17A shows the effect of treatment using radiotherapy, a nutritional supplement of the inventive concept, and combined treatment on expression of the VEGF gene 21 days after tumor cell injection. FIG. 17B shows the effect of treatment using radiotherapy, a nutritional supplement of the inventive concept, and combined treatment on expression of the BAX gene 21 days after tumor cell injection. FIG. 17C shows the effect of treatment using radiotherapy, a nutritional supplement of the inventive concept, and combined treatment on expression of the Bcl-2 gene 21 days after tumor cell injection. FIG. 17D shows the effect of treatment using radiotherapy, a nutritional supplement of the inventive concept, and combined treatment on expression of the Caspase 3 gene 21 days after tumor cell injection. FIG. 17E shows the effect of treatment using radiotherapy, a nutritional supplement of the inventive concept, and combined treatment on expression of the Bcl-2 gene 21 days in lung (i.e. metastasis) after tumor cell injection. FIG. 17F shows the effect of treatment using radiotherapy, a nutritional supplement of the inventive concept, and combined treatment on expression of the Caspase 3 gene 21 days in lung (i.e. metastasis) after tumor cell injection.

FIG. 18 depicts an alternative treatment/study protocol. FIG. 18 depicts a treatment/study protocol in which mice receive radiotherapy on days 8, 10, and 12, with nutritional supplementation provided for 7 days prior to tumor cell implantation. Mice are sacrificed at day 24 following implantation of tumor cells.

FIGS. 19A and 19B shows the results of studies of loss of body mass and muscle mass in mice treated with the protocol shown in FIG. 18. Statistically significant differences are indicated (* to ***). FIG. 19A shows the effect of treatment with a nutritional supplement of the inventive concept on body mass in mice receiving repeated radiotherapy following tumor cell implantation using the protocol shown in FIG. 18. FIG. 19B shows the effect of treatment using radiotherapy, a nutritional supplement of the inventive concept, and combined treatment on gastrocnemius muscle mass 21 days after tumor cell injection using the protocol shown in FIG. 18.

FIG. 20 depicts an alternative treatment/study protocol. FIG. 20 depicts a treatment/study protocol in which mice receive radiotherapy on days 8, 10, and 12, with nutritional supplementation provided for 7 days prior to, the day of, or 8 days after tumor cell implantation. Mice are sacrificed at day 21 following implantation of tumor cells.

FIG. 21 shows the effect of treatment with a nutritional supplement on body mass in mice receiving repeated radiotherapy following tumor cell implantation using the protocol shown in FIG. 20. Statistically significant differences are indicated (* to ***).

FIG. 22 shows changes in tumor volume over time on repeated radiotherapy in combination with treatment with a nutritional supplement of the inventive concept in mice treated as in the protocol shown in FIG. 20.

FIGS. 23A and 23B show the effect of the treatment protocol shown in FIG. 20 on serum concentration levels of pro-inflammatory cytokines in mice undergoing repeated radiotherapy treatments. FIG. 23A shows the effect of treatment using repeated radiotherapy, a nutritional supplement of the inventive concept, and combined treatment on serum TNF-α 21 days after tumor cell injection in mice treated using the protocol shown in FIG. 20. FIG. 23B shows the effect of treatment using repeated radiotherapy, a nutritional supplement of the inventive concept, and combined treatment on serum IL-6 21 days after tumor cell injection in mice treated using the protocol shown in FIG. 20.

DETAILED DESCRIPTION

Figure 1:
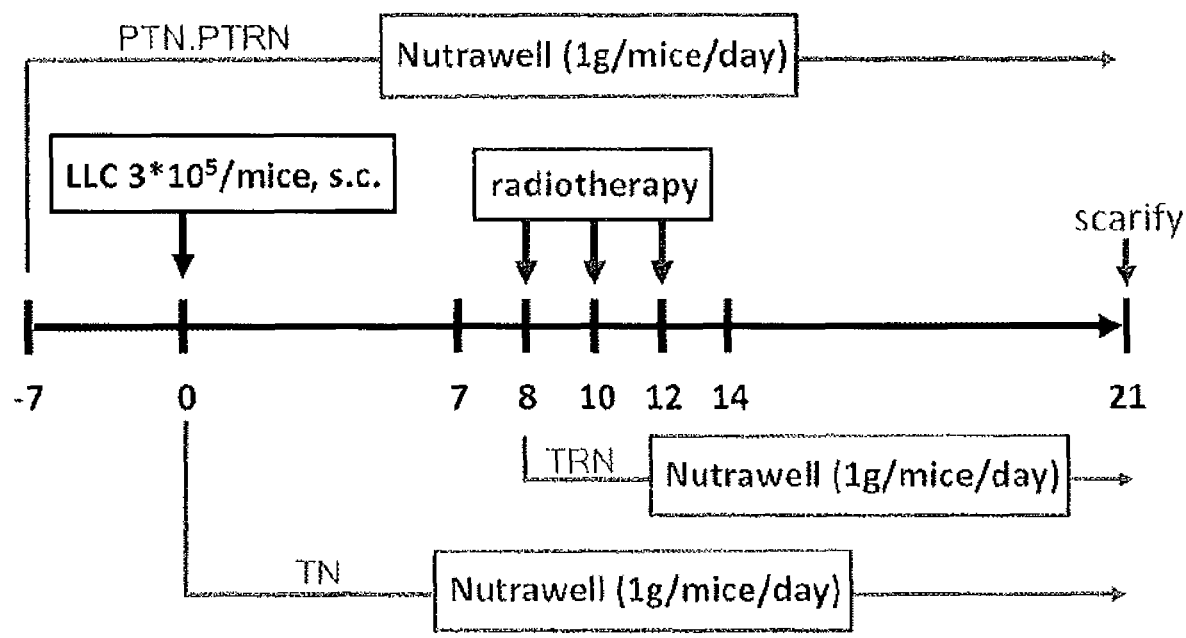
FIG. 1.

The following description includes information that may be useful in understanding the present invention. It is not an admission that any of the information provided herein is prior art or relevant to the presently claimed invention, or that any publication specifically or implicitly referenced is prior art.

The inventive subject matter provides compositions and methods in which a nutritional supplement (e.g. NutraWell) is used in combination with radiotherapy. Combination therapy with radiation and a nutritional supplement of the inventive concept surprisingly provides a significant synergistic effect in reduction of tumor size. In addition, side effects of radiotherapy (e.g. neutropenia, loss of body mass, loss of muscle mass, inflammation, damage to acyl cells of the gastrointestinal tract, etc.) are mitigated and expression of genes related to angiogenesis, pro-inflammatory cytokines, and apoptosis are modulated. In addition, metastasis is prevented and the growth and spread of cancer stem cells is reduced. The Inventors contemplate that similar benefits can be found in cotherapy with anti-cancer immunotherapy agents and a nutritional supplement of the inventive concept.

One should appreciate that the disclosed techniques provide many advantageous technical effects including enhancing the effectiveness of current radiotherapeutic protocols used in the treatment of cancer while reducing the side effects associated with these approaches.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In one embodiment of the inventive concept, a nutritional supplement composition of the inventive concept, such as shown in Table 1 (Nutrawell™), is provided to improve the results of radiotherapy.

TABLE 1

| Component | Minimum | Maximum | Unit |
|---|---|---|---|
| Maltodextrin | 10000 | 50000 | mg |
| Whey Protein Isolate | 5000 | 60000 | mg |
| Whey Protein Concentrate | 1000 | 50000 | mg |
| Fructooligosaccharides/Inulin | 40 | 15000 | mg |
| Granulated Honey | 1000 | 9000 | mg |
| Oat Fiber | 500 | 15000 | mg |
| Natural French Vanilla Flavor | 500 | 20000 | mg |
| Soy Protein | 500 | 50000 | mg |
| Brownulated Powdered Brown Sugar | 500 | 10000 | mg |
| Natural Vanilla Masking Flavor | 500 | 5000 | mg |
| Lecithin | 200 | 10000 | mg |
| Milk, Non-fat | 50 | 5000 | mg |
| Rice Protein Powder | 50 | 5000 | mg |
| Calcium Caseinate | 50 | 2000 | mg |
| Oils | | | |
| Flax Seed Oil | 100 | 7000 | mg |
| Canola Oil | 100 | 7000 | mg |
| Borage Oil | 100 | 7000 | mg |
| Olive Oil | 100 | 7000 | mg |
| Fish Oil | 150 | 10,000 | mg |
| Lemon Oil | 100 | 1000 | mg |
| Orange Oil | 50 | 1000 | mg |
| Mixed Tocopherols | 0.5 | 200 | mg |
| Vitamins/Minerals | | | |
| Potassium Phosphate | 200 | 1500 | mg |
| Calcium Carbonate | 100 | 5000 | mg |
| Choline Bitartrate | 150 | 2500 | mg |
| Sodium Chloride | 100 | 2000 | mg |
| Calcium Phosphate | 100 | 2000 | mg |
| Ascorbic Acid | 50 | 3000 | mg |
| Potassium Chloride | 50 | 2000 | mg |
| Magnesium Oxide | 50 | 500 | mg |
| Selenium Yeast | 30 | 4000 | mcg |
| Chromium Yeast | 30 | 3000 | mcg |
| Molybdenum Yeast | 30 | 2000 | mcg |
| Inositol | 10 | 5000 | mg |
| Zinc Sulfate | 5 | 200 | mg |
| Vitamin E | 5 | 2000 | IU |
| Niacinamide | 5 | 500 | mg |
| Ferric Orthophosphate | 3 | 100 | mg |
| Calcium Pantothenate | 3 | 200 | mg |
| Manganese Sulfate | 3 | 100 | mg |
| Beta Carotene | 1 | 100 | mg |
| Copper Gluconate | 1 | 15 | mg |
| Vitamin D3 | 25 | 5000 | IU |
| Vitamin K2 | 2 | 1000 | mcg |
| Pyridoxine | 0.5 | 200 | mg |
| Potassium Iodide | 0.5 | 1500 | mg |
| Riboflavin | 0.5 | 1000 | mg |
| Thiamine | 0.5 | 2500 | mg |

TABLE 1-continued

| Component | Minimum | Maximum | Unit |
|---|---|---|---|
| Vitamin K1 | 1 | 500 | mcg |
| Vitamin A Acetate | 500 | 100000 | IU |
| Folic Acid | 100 | 10000 | mcg |
| d-Biotin | 10 | 10000 | mcg |
| Vitamin B12 | 1 | 3000 | mcg |
| Amino Acids | | | |
| L-Carnitine | 300 | 30000 | mg |
| L-Glutamine | 500 | 60000 | mg |
| L-Arginine Base | 500 | 30000 | mg |
| Taurine | 50 | 2000 | mg |
| L-Lysine | 50 | 2000 | mg |
| Alpha Lipoic Acid | 10 | 1000 | mg |
| Resveratrol | 15 | 1500 | mg |
| Co-Enzyme Q10 | 10 | 5000 | mg |
| Glycine | 5 | 1000 | mg |
| Proline | 5 | 1000 | mg |
| Bacterial Cultures | | | |
| *Lact. Acidophilus* (app. 10 billion total) | 2 | 500 | mg |
| *Bifido Bifidium* (app. 10 billion total) | 2 | 500 | mg |
| *Lac. Bulgaricus* (app. 10 billion total) | 2 | 500 | mg |
| *Bifido Longum* (app. 10 billion total) | 2 | 500 | mg |
| *Strep. Thermophilus* (app. 10 billion total) | 2 | 500 | mg |
| Enzymes | | | |
| Papain | 5 | 100 | mg |
| Pepsin | 5 | 100 | mg |
| Lipase | 5 | 100 | mg |
| Bromelain | 5 | 100 | mg |
| Pancreatin | 0.5 | 100 | mg |
| Lactase | 1 | 100 | mg |
| Betaine | 3 | 100 | mg |
| Plant Products | | | |
| Pineapple Juice Powder | 2 | 500 | mg |
| Papaya Fruit Powder | 2 | 500 | mg |
| Quercetin | 30 | 3000 | mg |
| EGCG | 25 | 600 | mg |
| OPC | 15 | 500 | mg |
| Anthocyanins | 15 | 5000 | mg |
| Ellagic Acid | 10 | 300 | mg |
| Astaxanthin | 2 | 90 | mg |
| Fucoidan | 20 | 1500 | mg |
| Mushroom Preparation | | | |
| *Cordyceps* | 5 | 6000 | mg |
| *Ganoderma Lucidum* | 15 | 10000 | mg |
| Shiitake | 40 | 15000 | mg |
| Maitake | 30 | 15000 | mg |
| Turkey Tail | 30 | 15000 | mg |

The composition shown in Table 1 includes components that have various physiological and biochemical effects, including anti-inflammatory activity, lowering of blood glucose levels, lowering of cholesterol, and anti-tumor activity. Other components provide supplementation of necessary vitamins, minerals, and amino acids at elevated levels. Other components (e.g. enzymes, lecithin) serve to aid in digestion and absorption of components of the composition when consumed. The combination of these complementary activities provides a synergistic effect that exceeds the simple additive effect of individual components. It should be appreciated that the composition shown in Table 1 also includes certain flavorants (e.g. brown sugar, honey, vanilla flavor and/or masking agent) that serve to improve palatability and acceptance. Certain components (e.g. honey, brown sugar, milk, rice protein, casein) can provide both flavor and caloric energy. The Inventor has found that the combination of flavorants described above is effective in providing compliance with consumption of the nutritional supplement in effective amounts. In some embodiments such flavorants can be excluded from the formulation without negatively impacting the effectiveness of the nutritional supplement, thereby providing a functional nutritional supplement that includes only essential components. It should be appreciated that components of a nutritional supplement of the inventive concept can be provided as powders, granules, liquids, suspensions, and/or emulsions. In a preferred embodiments components of the nutritional supplement are provided as powders and/or granules. Similarly, in preferred embodiments of the inventive concepts components of the nutritional supplement are provided in relative amounts as indicated in Table 1. In some embodiments the components of the nutritional supplement are provided as a single, mixed formulation. In other embodiments components of the nutritional supplement can be provided as a kit or similar assembly containing different components of the formulation segregated or packaged separately (for example, to provide different storage conditions conducive to component stability).

It should be appreciated that oils found in the formulation (e.g. Flax Seed Oil, Canola Oil, Borage Oil, Olive Oil, Fish Oil, Pure Lemon Oil, Pure Orange Oil, Mixed Tocopherols) are at least consumer grade, and preferably highly purified (>95% pure). It should also be appreciated that mineral components (e.g. potassium, calcium, sodium, magnesium iron, manganese) can be provided as any safe and absorbable salt (e.g. a halide salt, phosphate salt, carbonate salt, sulfate salt), oxide, or organic complex (e.g. gluconate). It should also be appreciated that certain metals (e.g. chromium, molybdenum, selenium) are supplied in the form of a yeast component, which can include provision as a yeast-containing powder or suspension and/or as a complex with a peptide or amino acid as a result of metabolism of such metals by yeast. Similarly, it should be appreciated that preparation of various non-yeast fungi (e.g. *Cordyceps, Ganoderma Lucidum, Shiitake, Maitake*, Turkey Tail) can include powdered or granular preparation derived from dried/lyophilized fruiting bodies of such fungi.

A nutritional supplement of the inventive concept can be provided in amounts ranging from about 1 mg/kg body weight to about 100 g/kg body as a unit dose. Such a unit dose can be provided on a schedule ranging from 4 times a day to one time per week. The nutritional supplement can be provided as one or more pills or capsules. Alternatively the nutritional supplement can be provided as a powder, granular, and/or liquid formulation that is added to a food or a beverage prior to consumption. In some embodiments the nutritional supplement can be provided as a food item, such as a food or candy bar. In other embodiments the nutritional supplement can be provided as a solution, suspension, or beverage that is suitable for oral consumption and/or provision by tube feeding.

It should be appreciated that packaging that excludes light, moisture, and/or oxygen can be used to extend the shelf life of the nutritional supplement. Similarly, a nutritional supplement of the inventive concept can be packaged with a hygroscopic agent (such as silica gel), a non-reactive gas (such as N2 or a noble gas), and/or under vacuum in order to extend shelf life. Such packaging can, for example, provide a nutritional supplement of the inventive concept in single unit doses and additionally provide directions for preparation and/or dosing frequency.

In studies to determine the effect of combined radiotherapy and treatment with a nutritional supplement of the inventive concept mice carrying human tumor cells (following transplantation into nude mice) were treated with 1 gram per day of the nutritional supplement, radiotherapy, or 1 gram per day of the nutritional supplement and chemotherapy. The mice were weighed during treatment to characterize side effects such as nausea and loss of appetite. In some studies blood samples were taken to determine values for certain serum and cellular components. After several weeks the mice were sacrificed and tumor (and, in some cases, certain muscles and organs) characterized. For example, tumor volume was determined and the impact of therapy on organ and muscle volume was determined. The degree of neutropenia was also characterized. A typical set of test groups is shown in Table 2.

TABLE 2

| | | | Sacrifice (21$^{st}$ day) |
|---|---|---|---|
| 1 | C | Control | N = 6 |
| 2 | T | Tumor | N = 6 |
| 3 | PTN | Tumor + Nutrawell (−7 day start) | N = 6 |
| 4 | TN | Tumor + Nutrawell (0 day start) | N = 6 |
| 5 | TR | Tumor + Radiotherapy (3 Gy X 3) | N = 6 |
| 6 | PTRN | Tumor + Radiotherapy (3 Gy X 3) + Nutrawell (−7 day start) | N = 6 |
| 7 | TRN | Tumor + Radiotherapy (3 Gy X 3) + Nutrawell (8 day start) | N = 6 |

A typical treatment schedule is depicted schematically in FIG. 1. In this treatment protocol nutritional supplementation is provided starting either 7 days prior to implementation of radiotherapy or simultaneously with tumor cell implantation. Mice were sacrificed 21 days after tumor cell implantation.

Figure 2A:
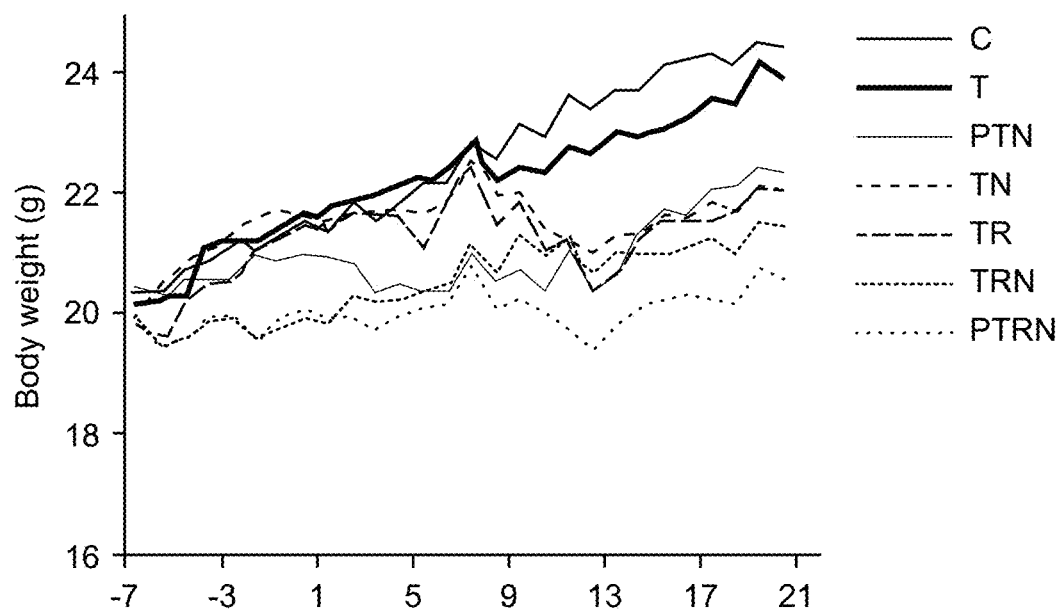
FIGS. 2A and 2B.
Figure 2B:
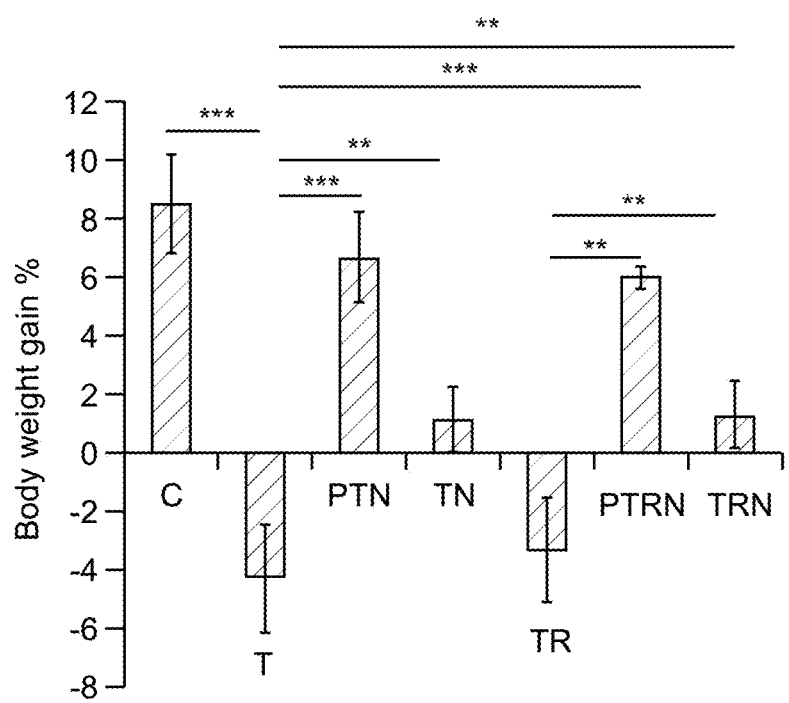

Results of body weight studies resulting from such a protocol are shown in FIGS. 2A and 2B. As shown, mice receiving both radiotherapy and a nutritional supplement of the inventive concept gained weight at a significantly greater rate than those receiving only radiotherapy, indicating a reduction in undesirable side effects normally associated with this treatment mode.

Figure 3A:
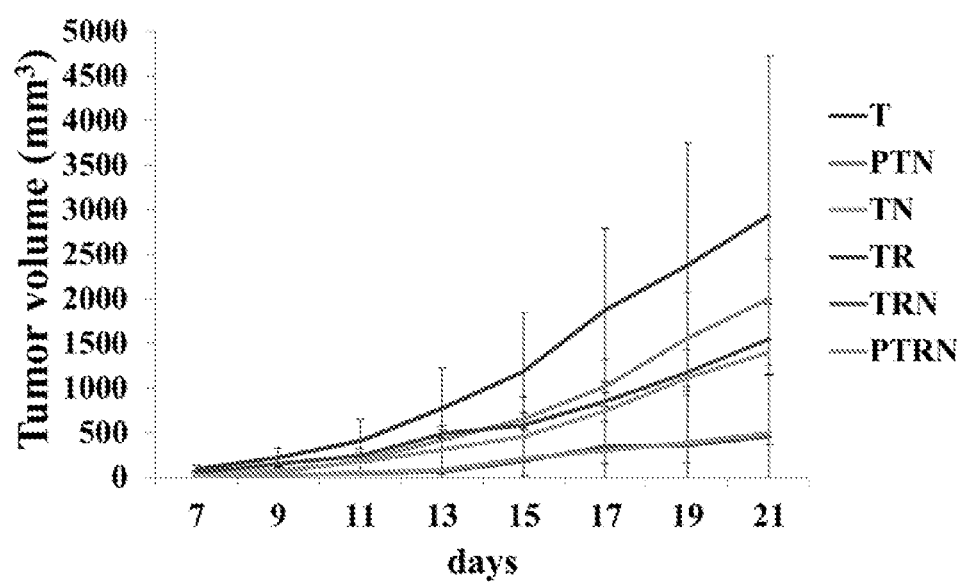
FIGS. 3A to 3D.
Figure 3B:
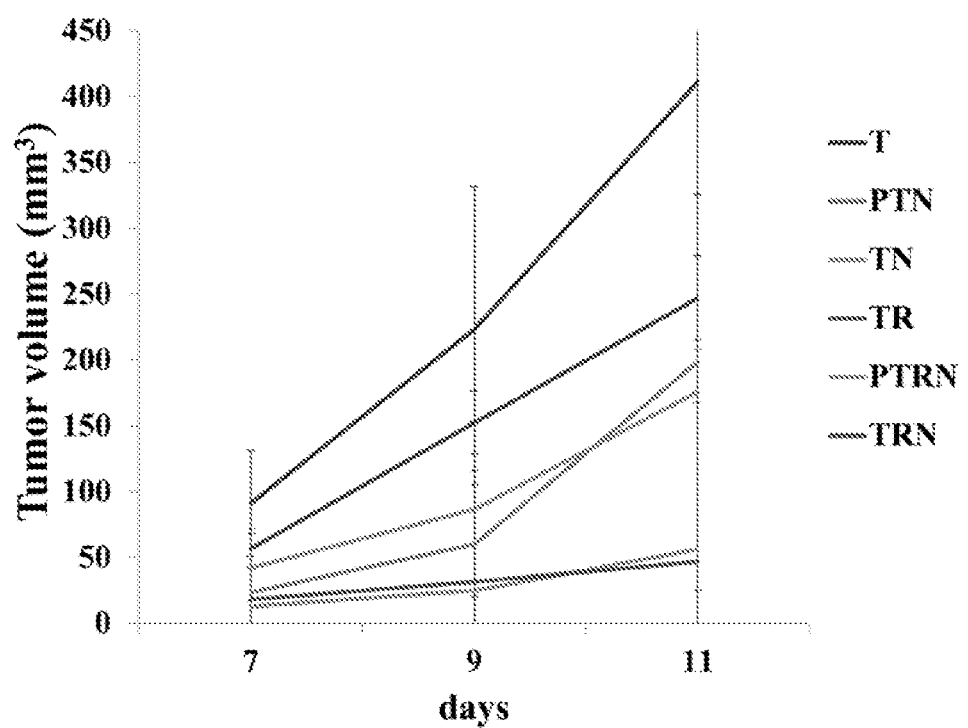
Figure 3C:
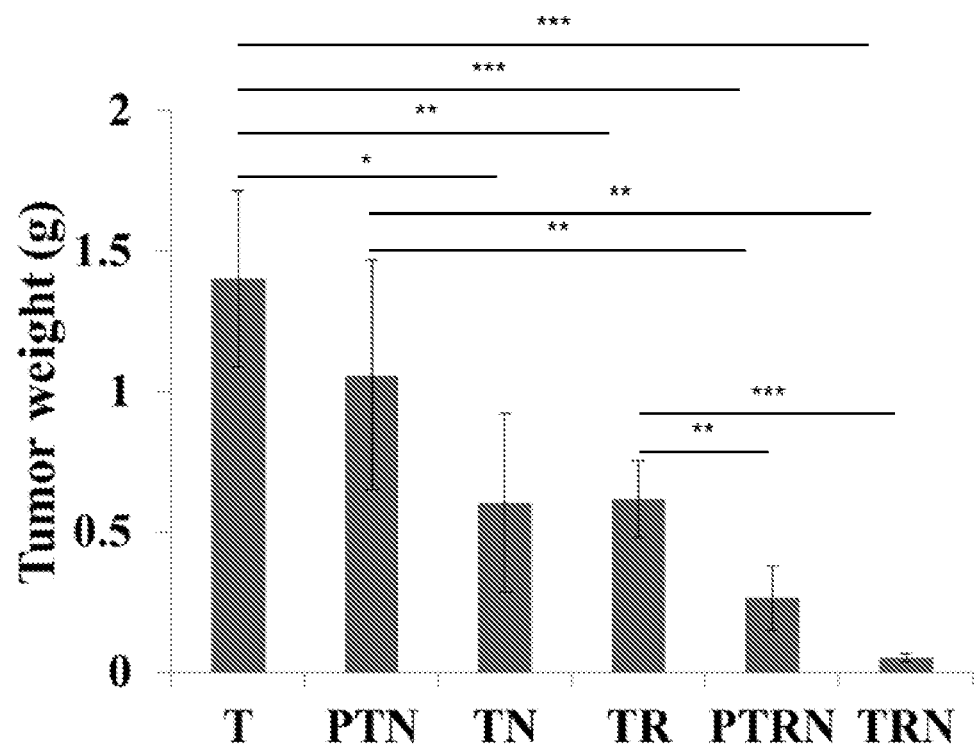
Figure 3D:
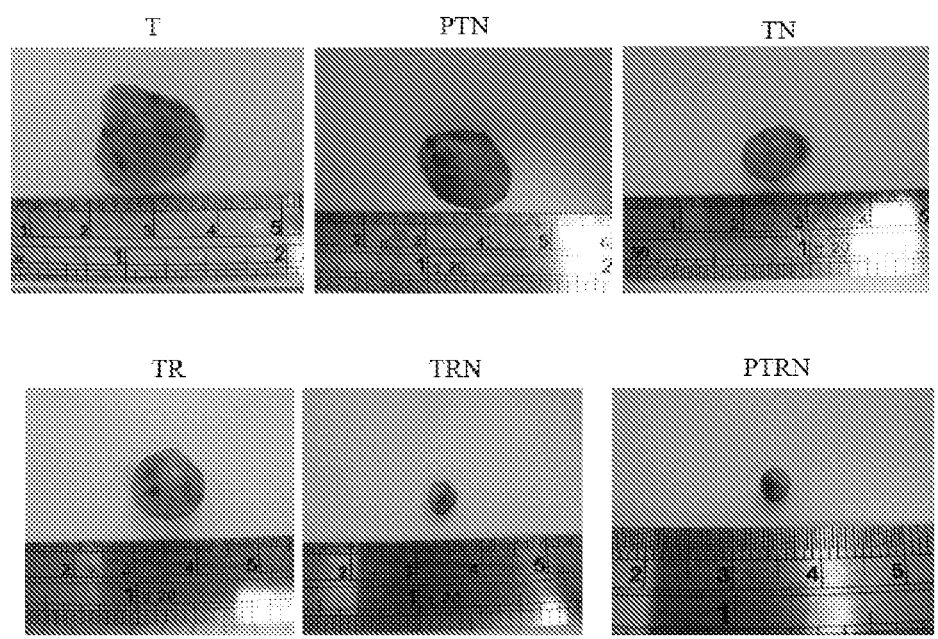
Figure 4A:
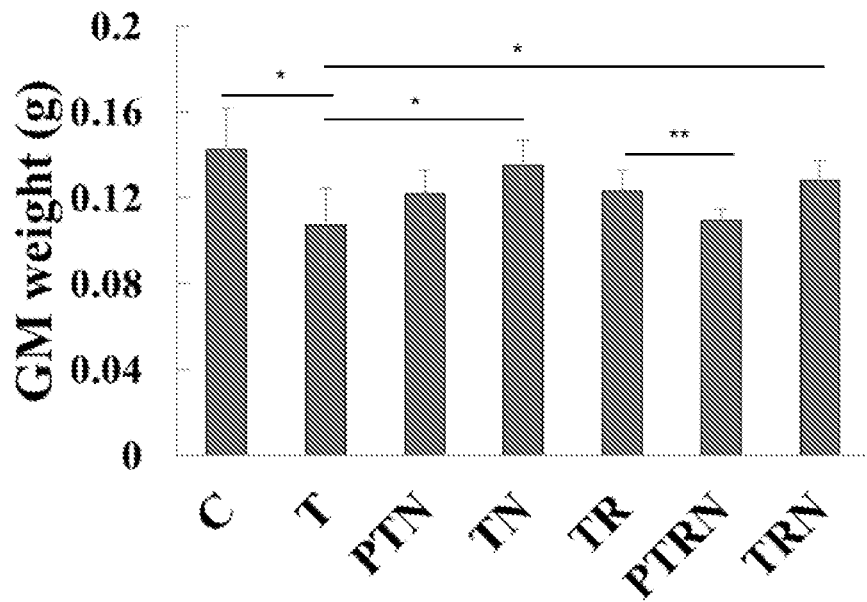
FIGS. 4A to 4E.
Figure 4B:
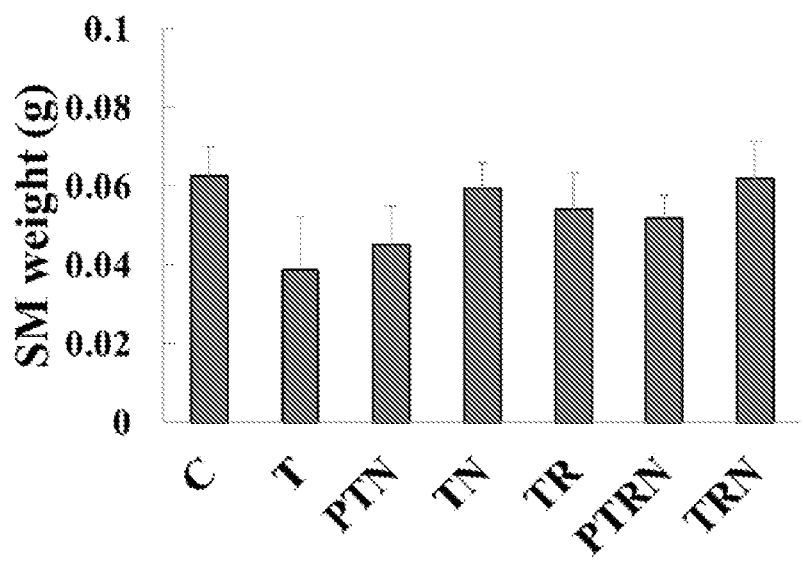
Figure 4C:
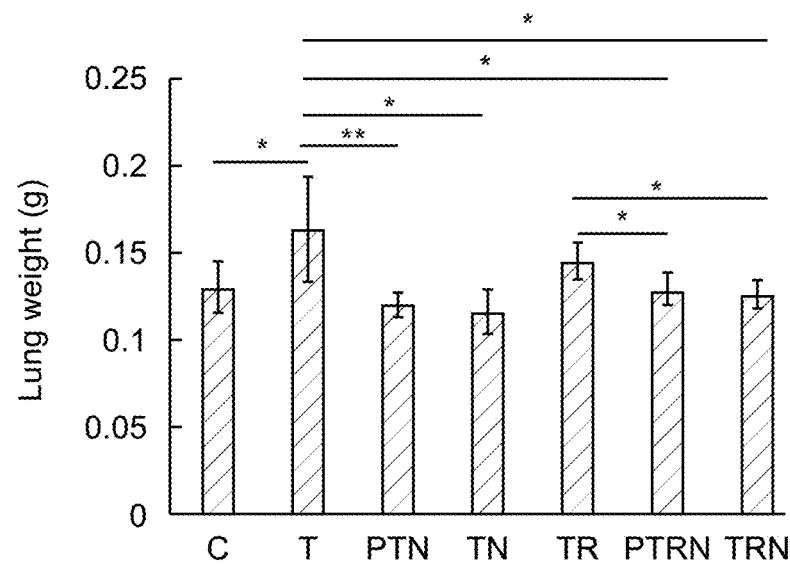
Figure 4D:
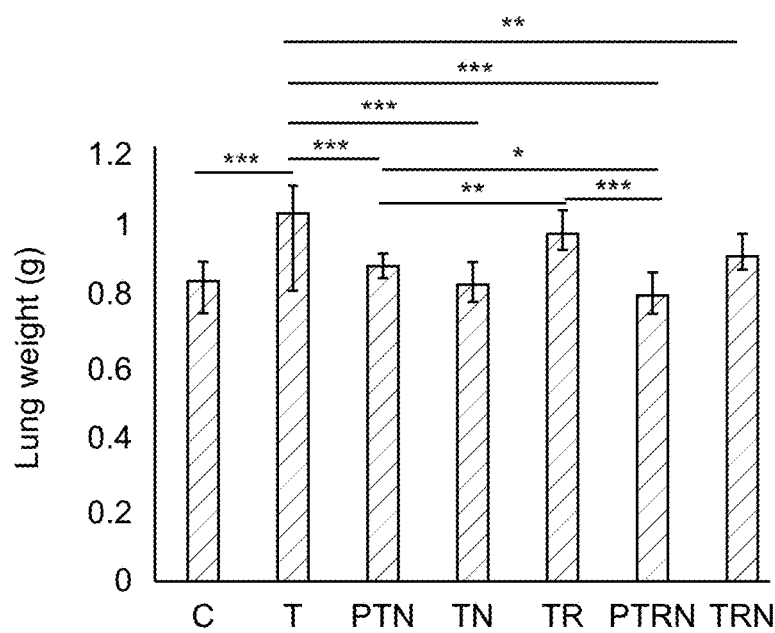
Figure 4E:
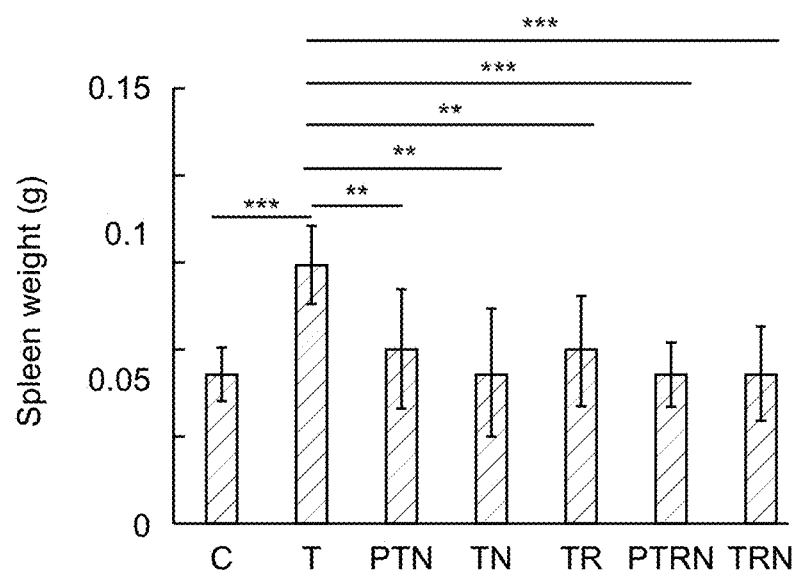
Figure 5A:
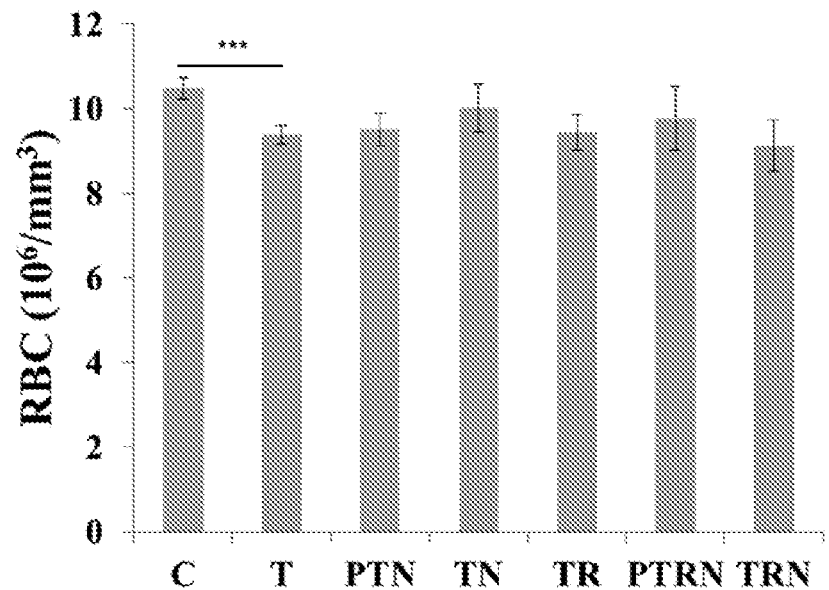
FIGS. 5A to 5G.
Figure 5B:
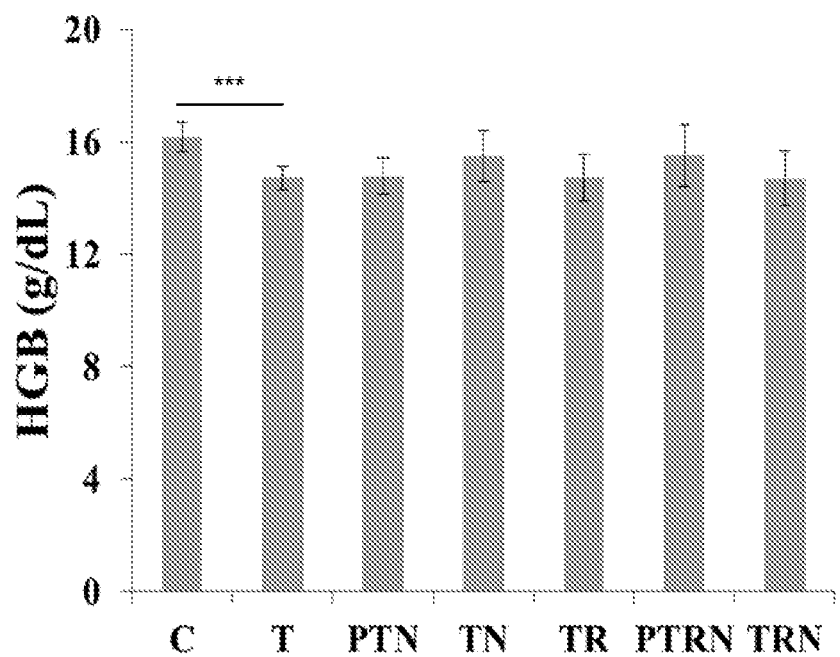
Figure 5C:
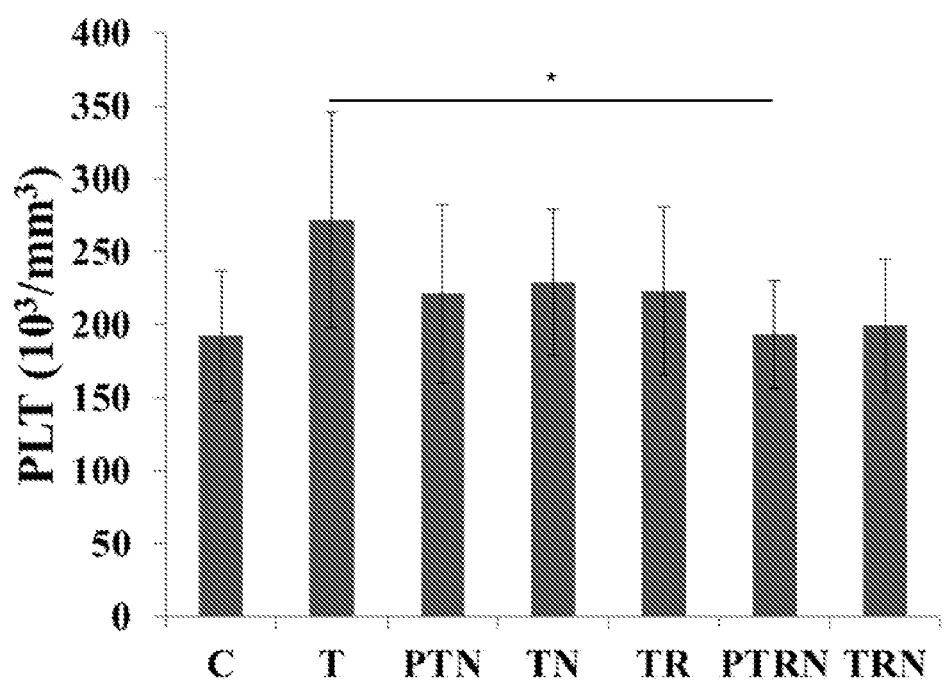
Figure 5D:
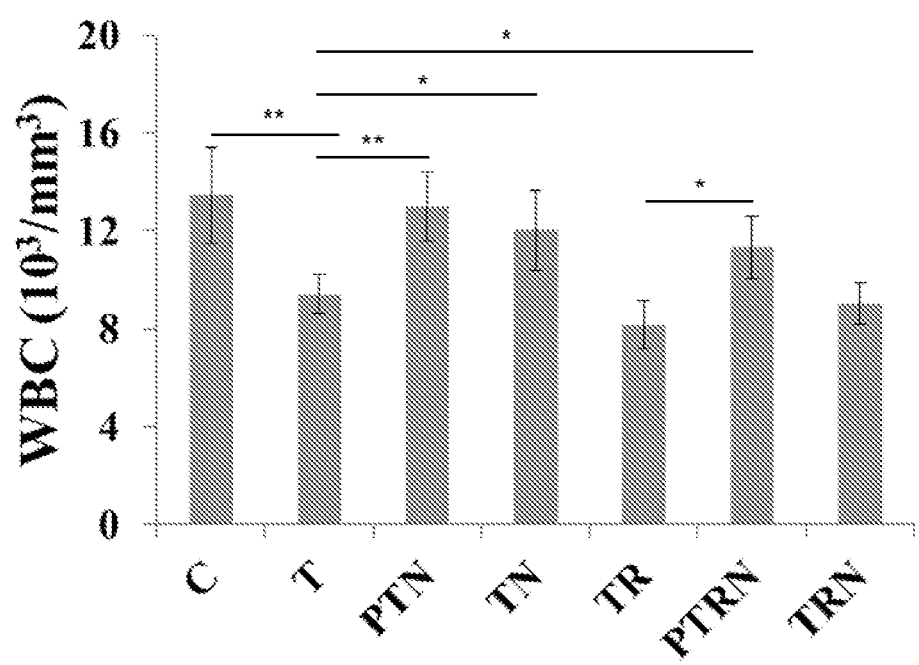
Figure 5E:
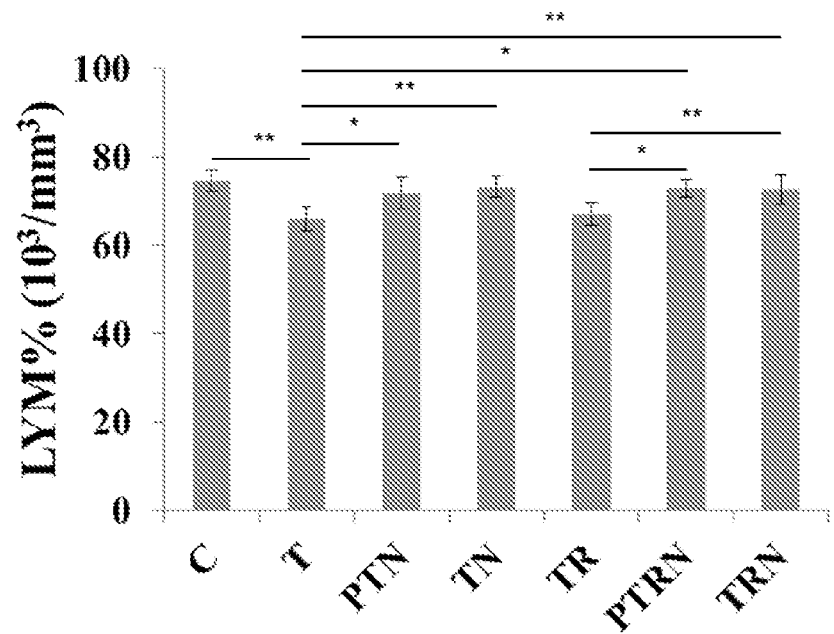
Figure 5F:
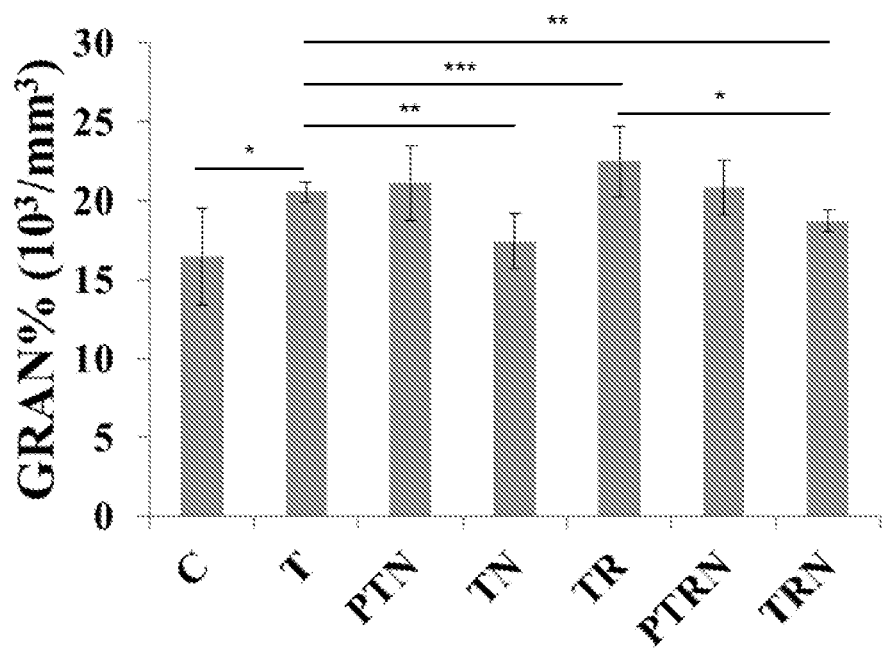
Figure 5G:
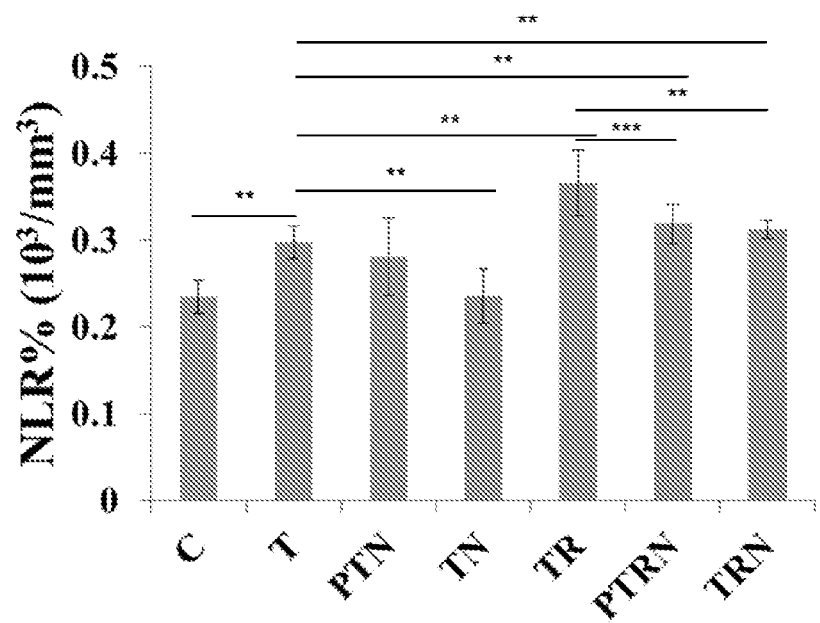
Figure 6A:
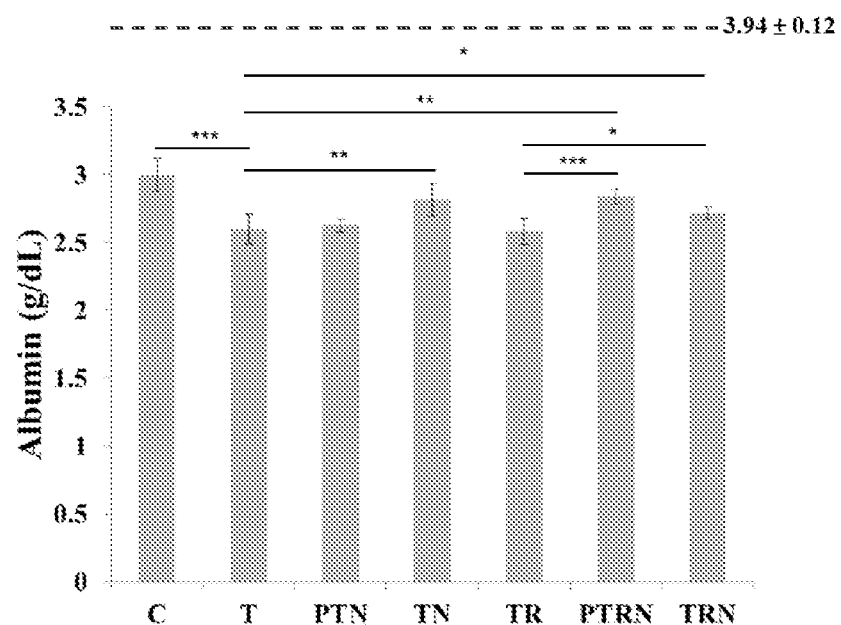
FIGS. 6A to 6G.
Figure 6B:
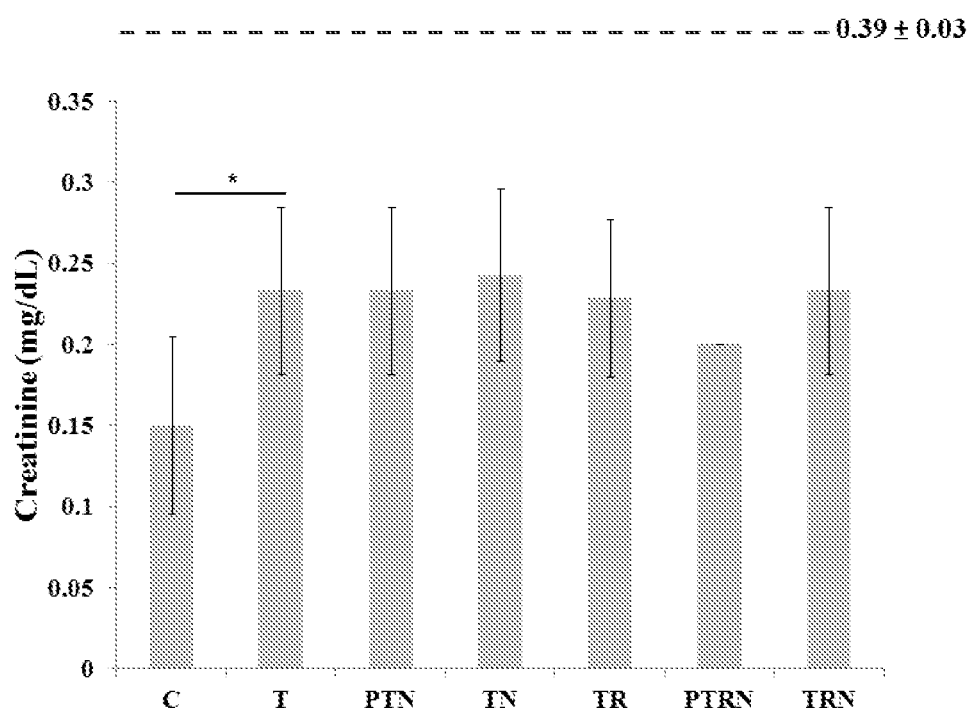
Figure 6C:
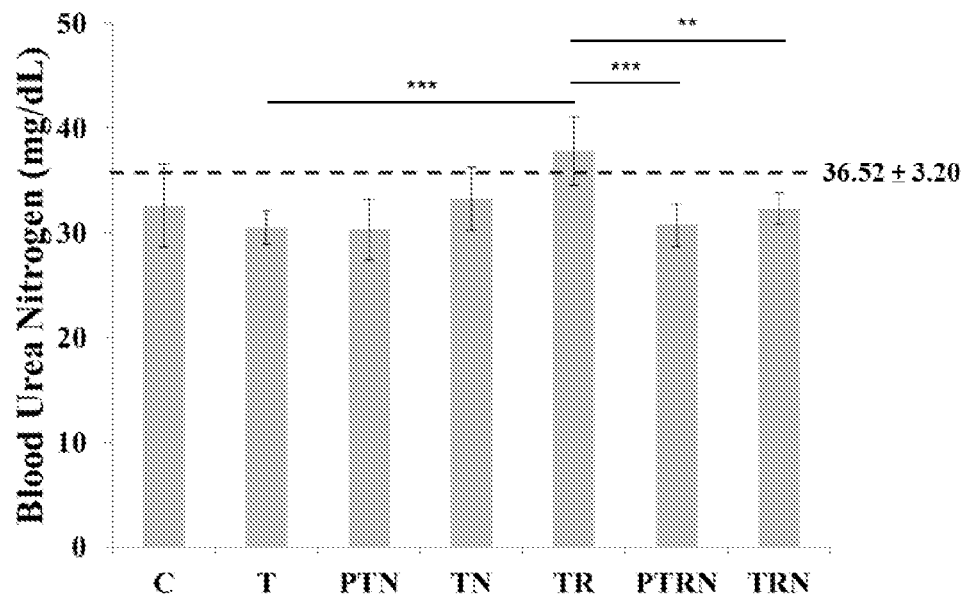
Figure 6D:
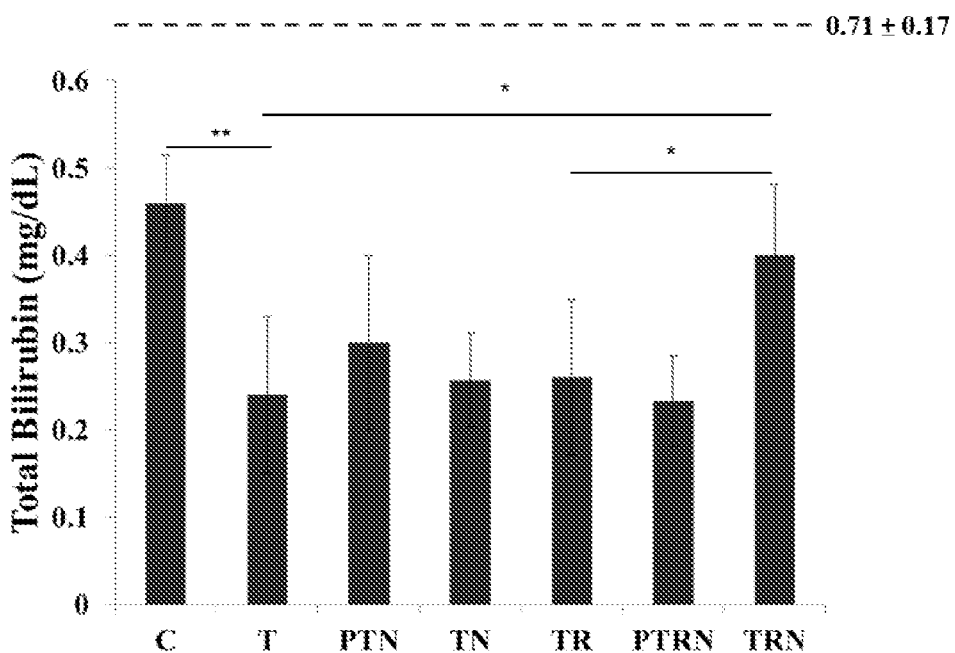
Figure 6E:
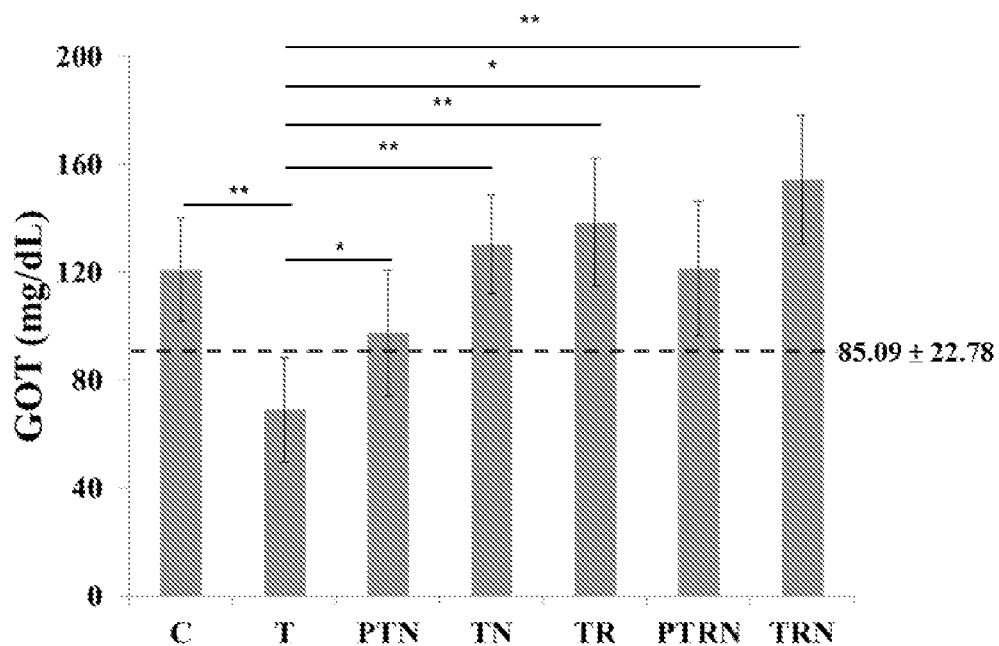
Figure 6F:
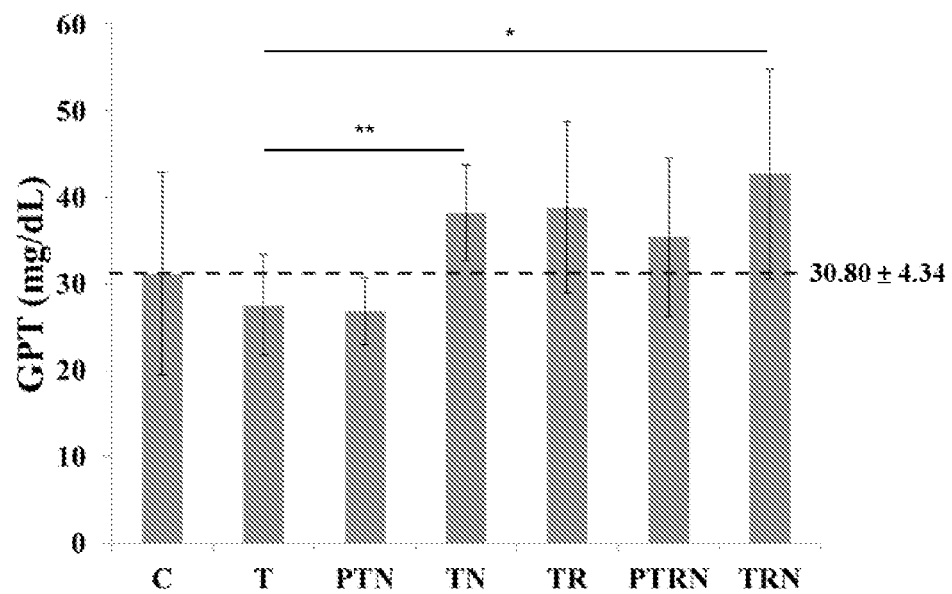
Figure 6G:
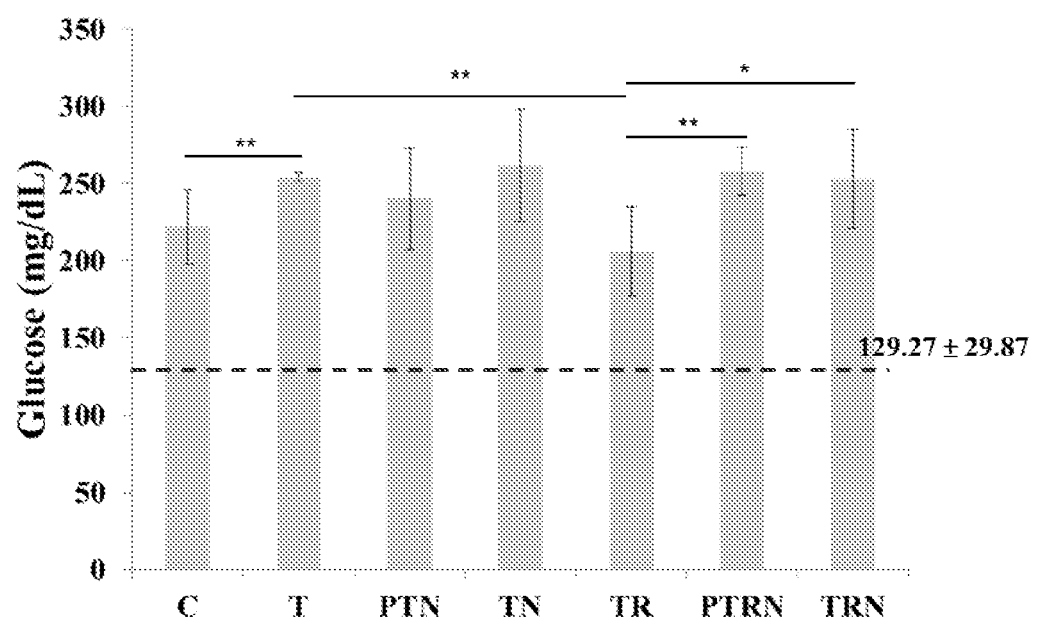

FIGS. 3A to 3D show typical synergistic effects on tumor volume and weight of co-treatment with radiotherapy and a nutritional supplement of the inventive concept. FIG. 3A shows the effect of various treatment protocols on tumor volume over the course of 3 weeks, with FIG. 3B providing an scaled view of the effect over the initial 11 days. As shown, treatment with the nutritional supplement alone provides an approximately 60% reduction in tumor volume. Treatment with radiation alone provides a similar reduction in tumor volume. In the absence of a synergistic effect one would therefore anticipate a reduction in tumor volume to approximately 25% of that of the untreated tumor. Surprisingly, what is observed is a greater than 90% reduction in tumor volume to approximately 7% of the untreated tumor-indicative of a significant synergistic effect.

Side effects of radiotherapy go beyond loss of appetite and weight loss, and can include damage to internal organs, loss of muscle mass, anemia, neutropenia, reduction in kidney function, etc. To determine the protective effects of nutritional supplement/radiotherapy cotherapy in regards to such side effects on muscle mass and organ weight of treated mice were also characterized following therapy. The results are shown in FIGS. 4A to 4E. Similarly, the effects of this cotherapy on various blood cell populations are shown in FIGS. 5A to 5G. The effects of radiotherapy cotherapy with a nutritional supplement of the inventive concept on various serum biochemistry markers, which provide information regarding kidney function, liver function, and/or nutritional status are shown in FIGS. 6A to 6G. As shown, nutritional supplement of the inventive concept is effective in reducing the negative impact of radiotherapy.

Figure 7A:
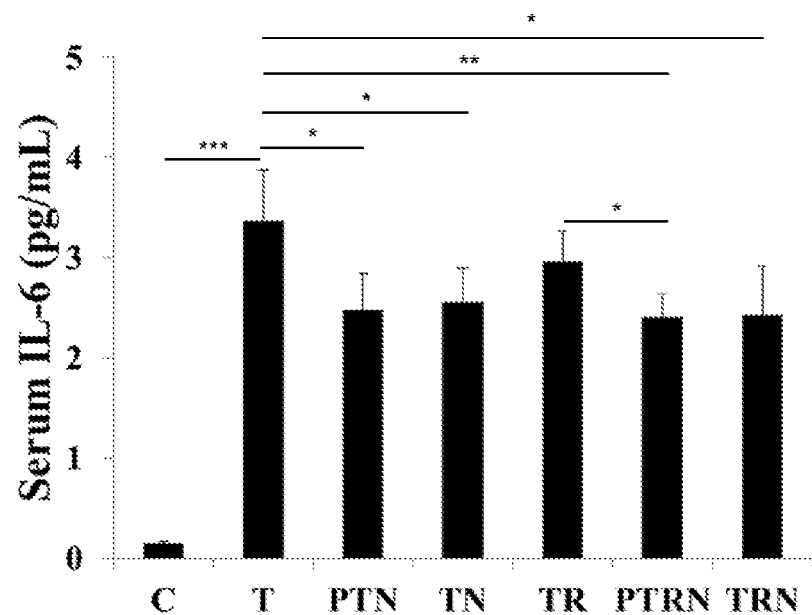
FIGS. 7A and 7B.
Figure 7B:
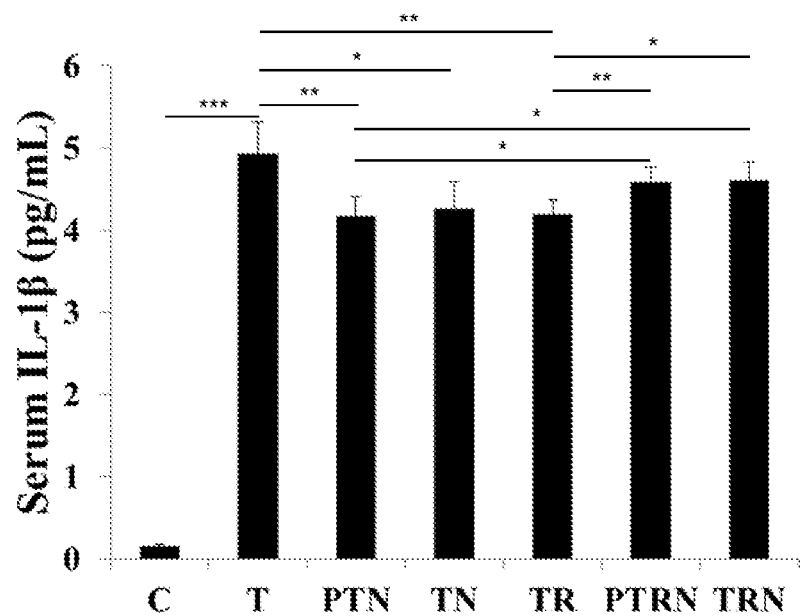
Figure 8A:
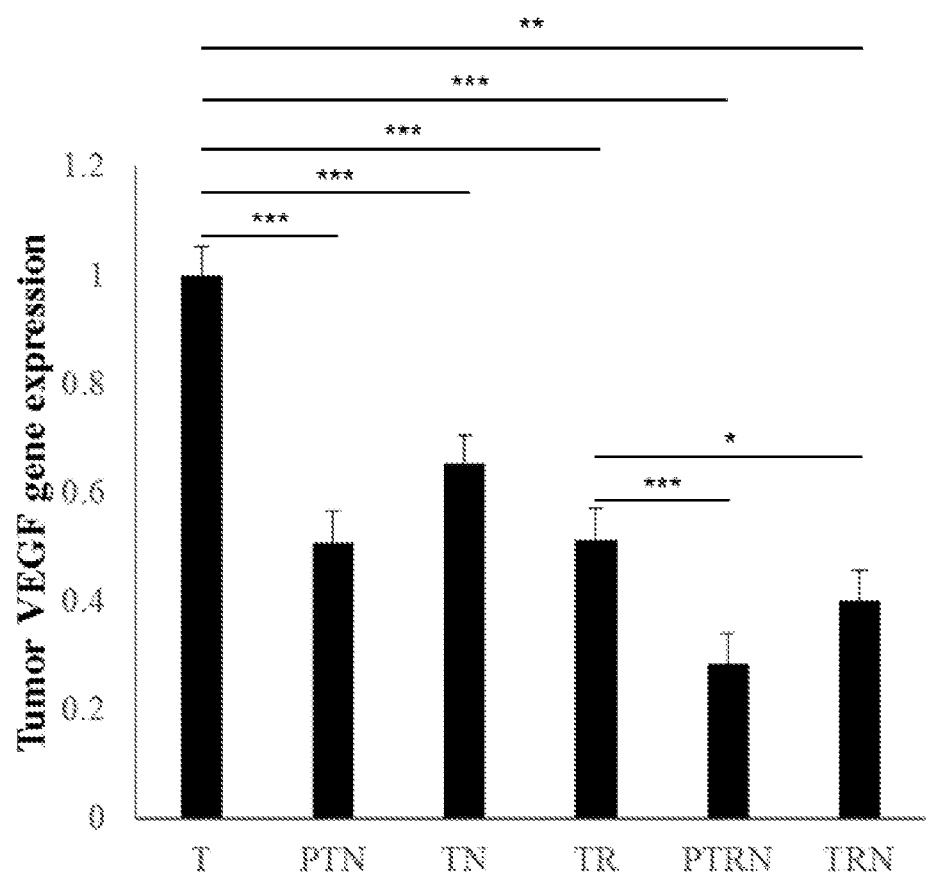
FIGS. 8A to 8G.
Figure 8B:
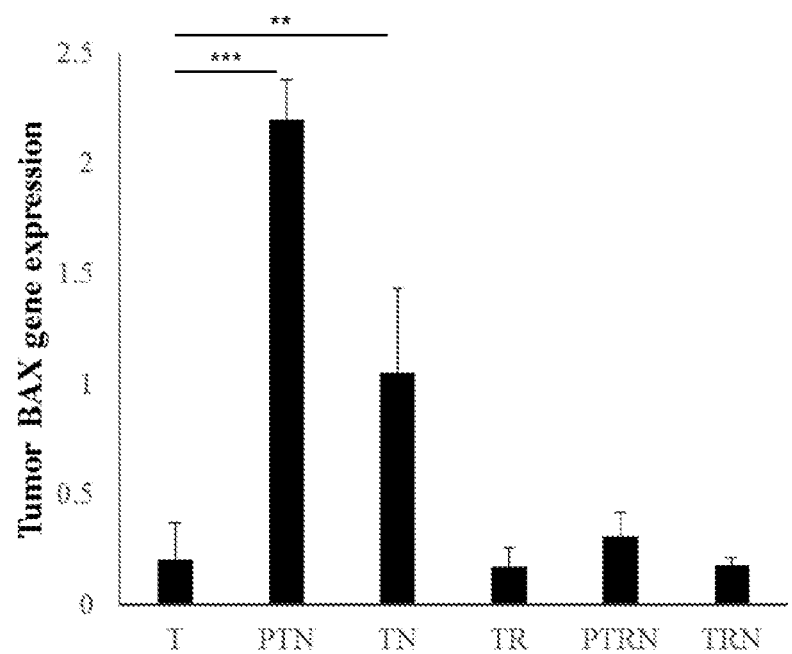
Figure 8C:
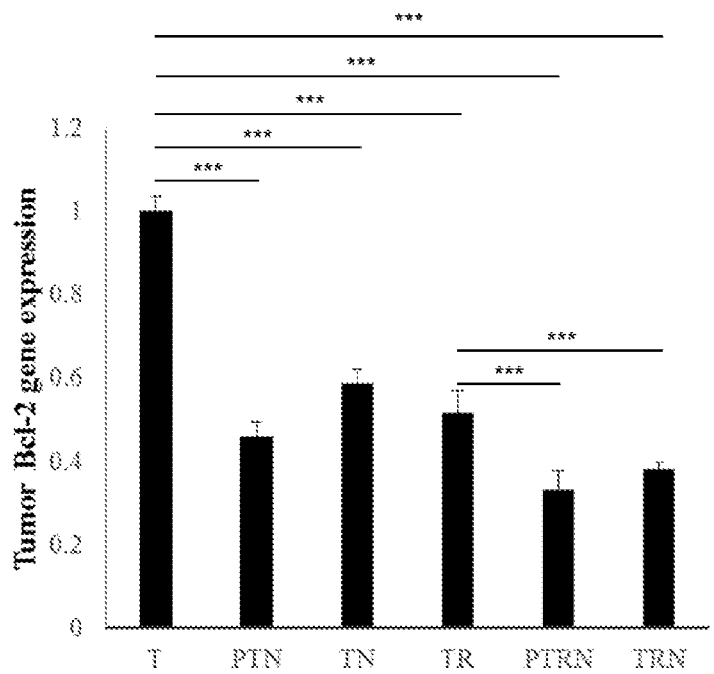
Figure 8D:
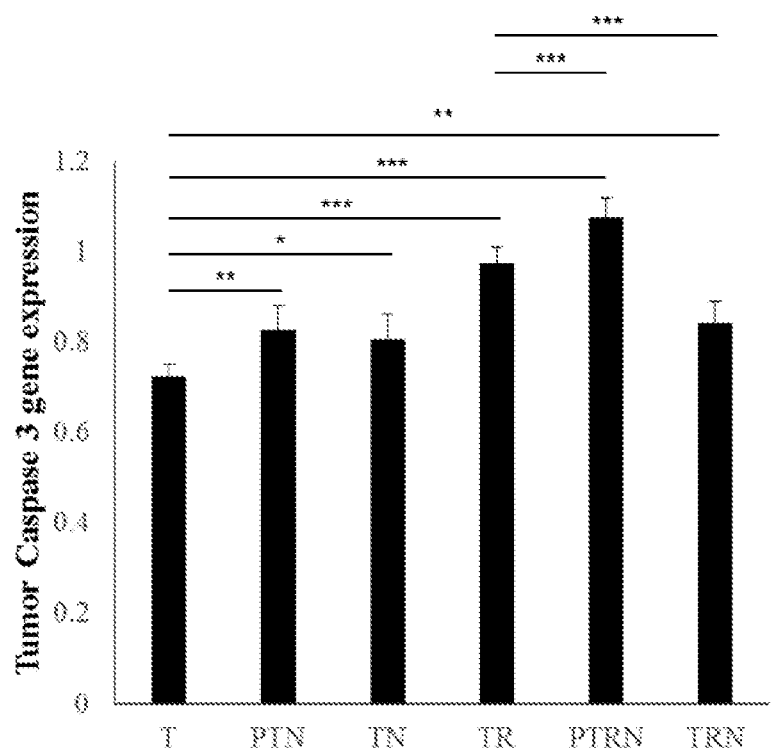
Figure 8E:
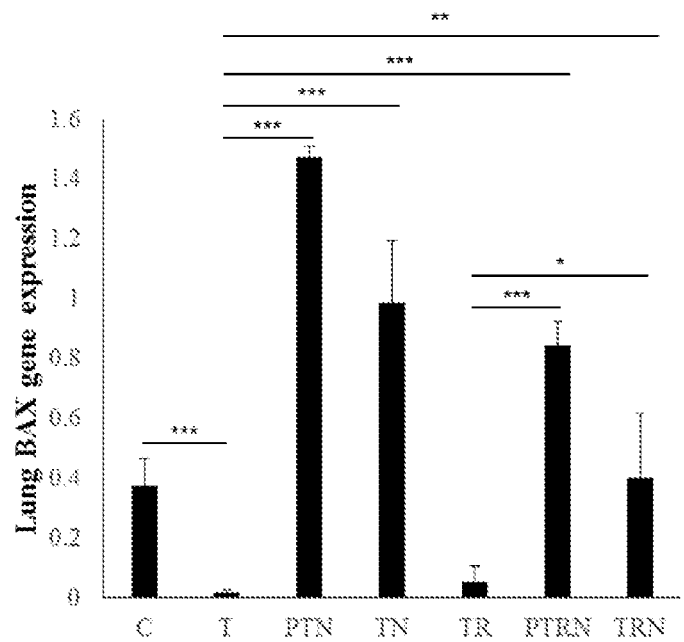
Figure 8F:
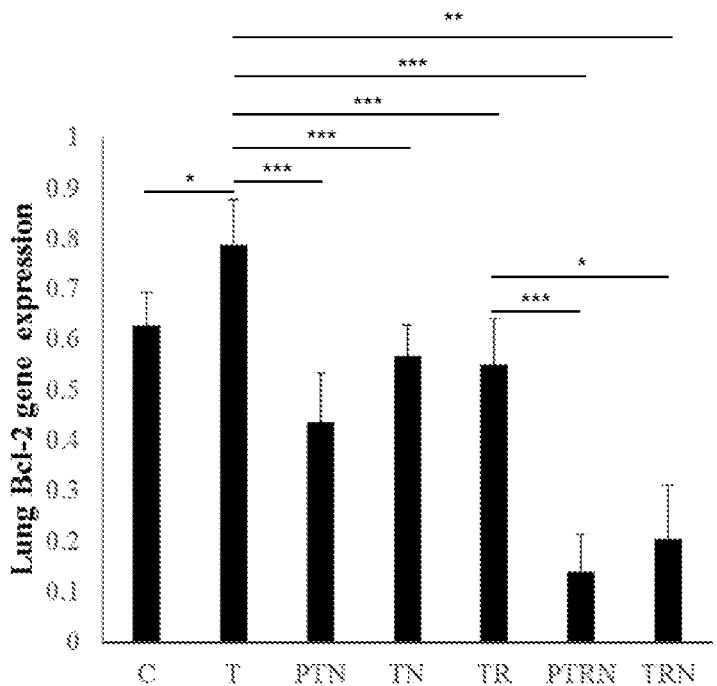
Figure 8G:
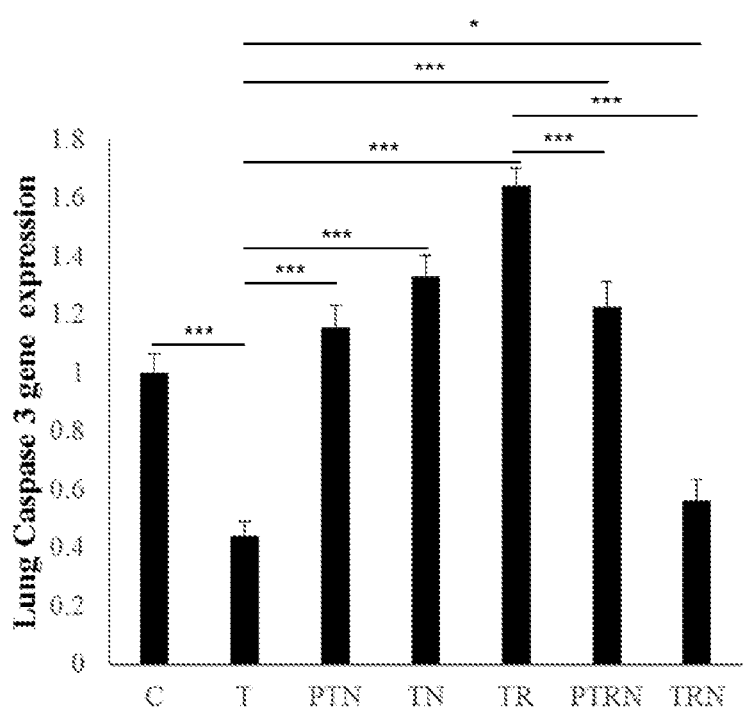

The growth and spread of tumors is associated with inflammation, as is the application of radiotherapy. Surprisingly, Inventors have found that cotreatment with a nutritional supplement of the inventive concept is effective in reducing the concentration of pro-inflammatory cytokines, indicating that such co-treatment is effective in reducing inflammation associated with tumors, and with radiotherapy of tumors. The effects of nutritional supplement of the inventive concept on serum concentrations of pro-inflammatory cytokines is shown in FIGS. 7A and 7B, and show marked reductions in pro-inflammatory cytokines.

Surprisingly, Inventors have also found that treatment with nutritional supplement of the inventive concept can modify gene expression in tumor cells in vivo, and can provide a synergistic effect to such changes in gene expression resulting from radiotherapy. In some embodiments the genes are related to cytokines and/or are related to apoptosis. Examples of the effect of radiotherapy, treatment with nutritional supplement of the inventive concept, and cotherapy on gene expression in implanted tumor cells in vivo are shown in FIG. 8A to 8F. As shown gene expression is (at least to some extent) normalized in tumor cells of mice so treated.

Figure 9:
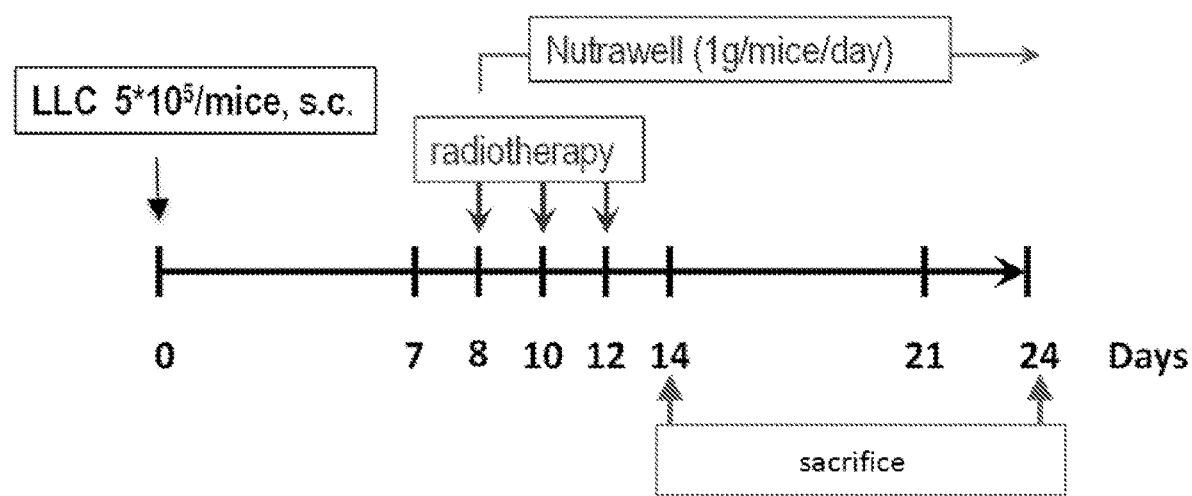
FIG. 9.

Similar studies were performed using modified treatment protocols. One such modified treatment protocol utilizing multiple rounds of radiotherapy is shown in FIG. 9. Treatment groups derived from the protocol shown in FIG. 9 are summarized in Table 3.

TABLE 3

| | | | Sacrifice (14$^{th}$ day) | Sacrifice (24$^{th}$ day) |
|---|---|---|---|---|
| 1 | C | Control | N = 6 | N = 6 |
| 2 | T | Tumor | N = 6 | N = 6 |
| 3 | TN | Tumor + Nutrawell | N = 6 | N = 6 |
| 4 | T3R | Tumor + Radiotherapy (X3) | N = 6 | N = 6 |
| 5 | T3RN | Tumor + Radiotherapy (X3) + Nutrawell | N = 6 | N = 6 |

Figure 10A:
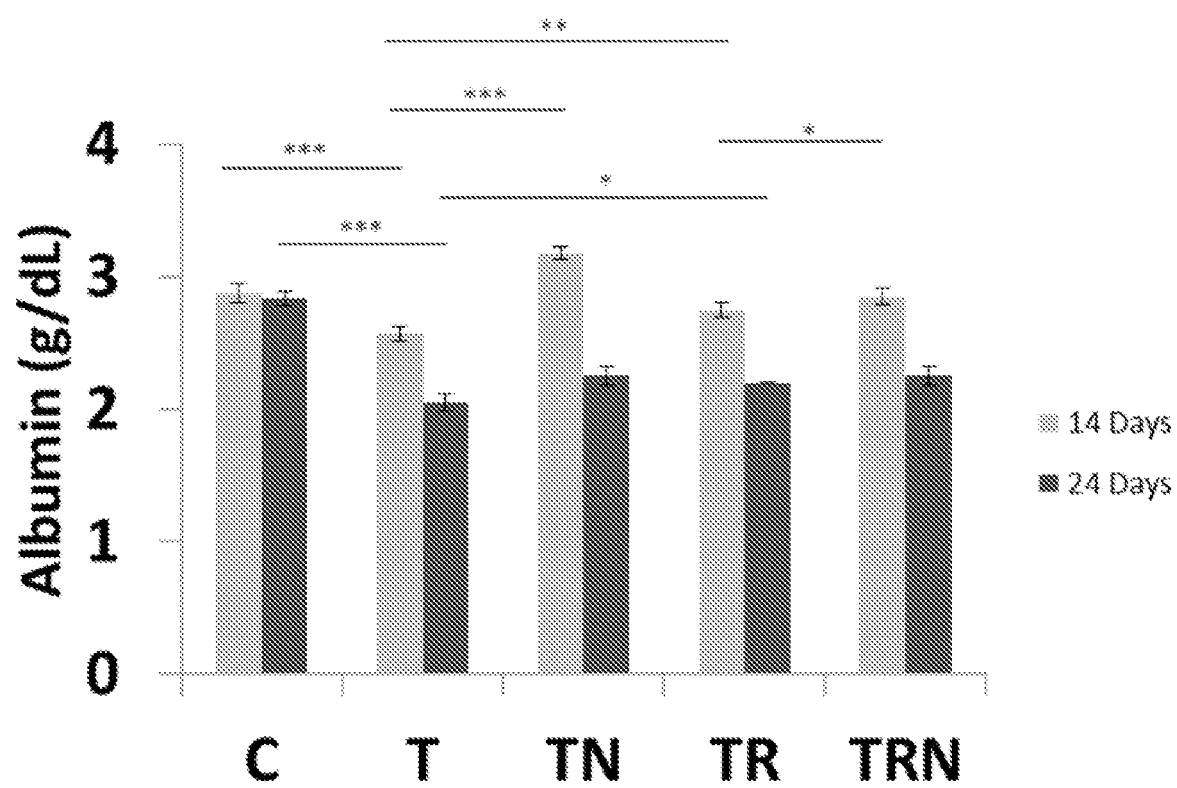
FIGS. 10A to 10C.
Figure 10B:
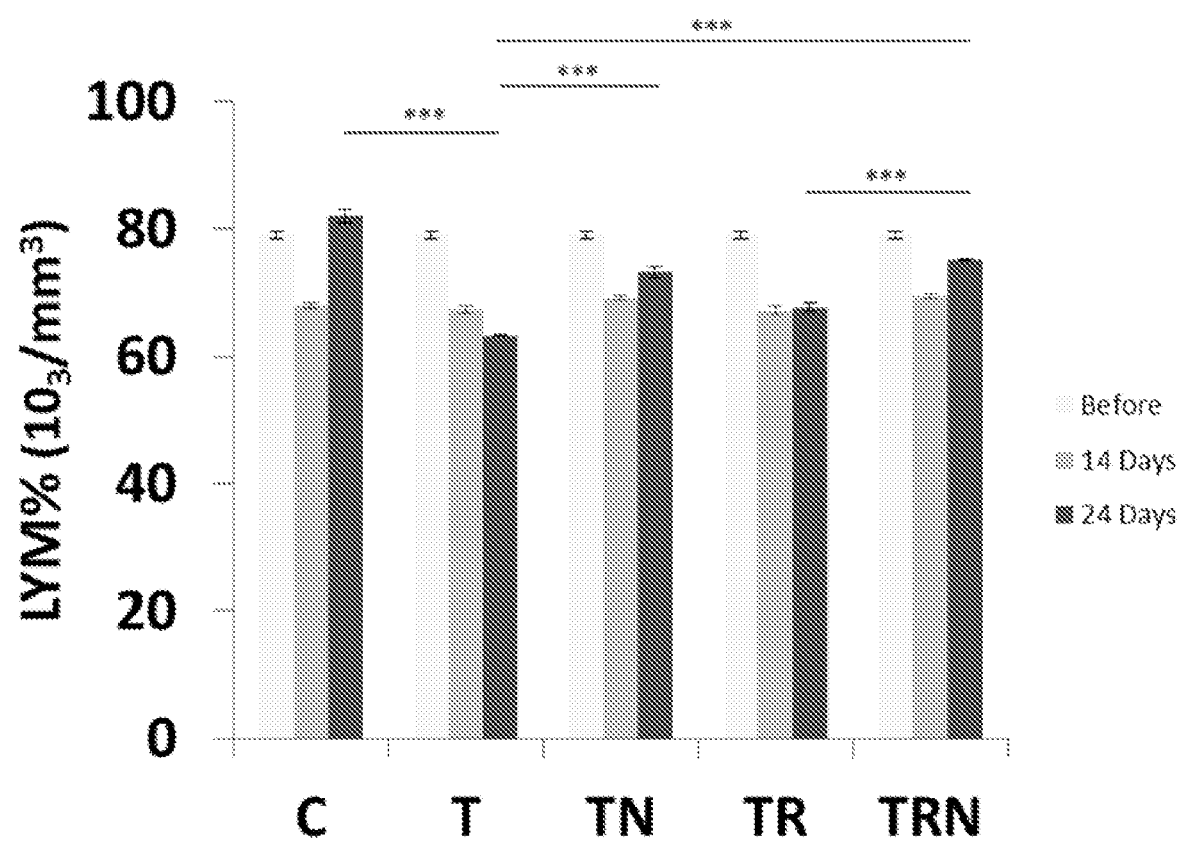
Figure 10C:
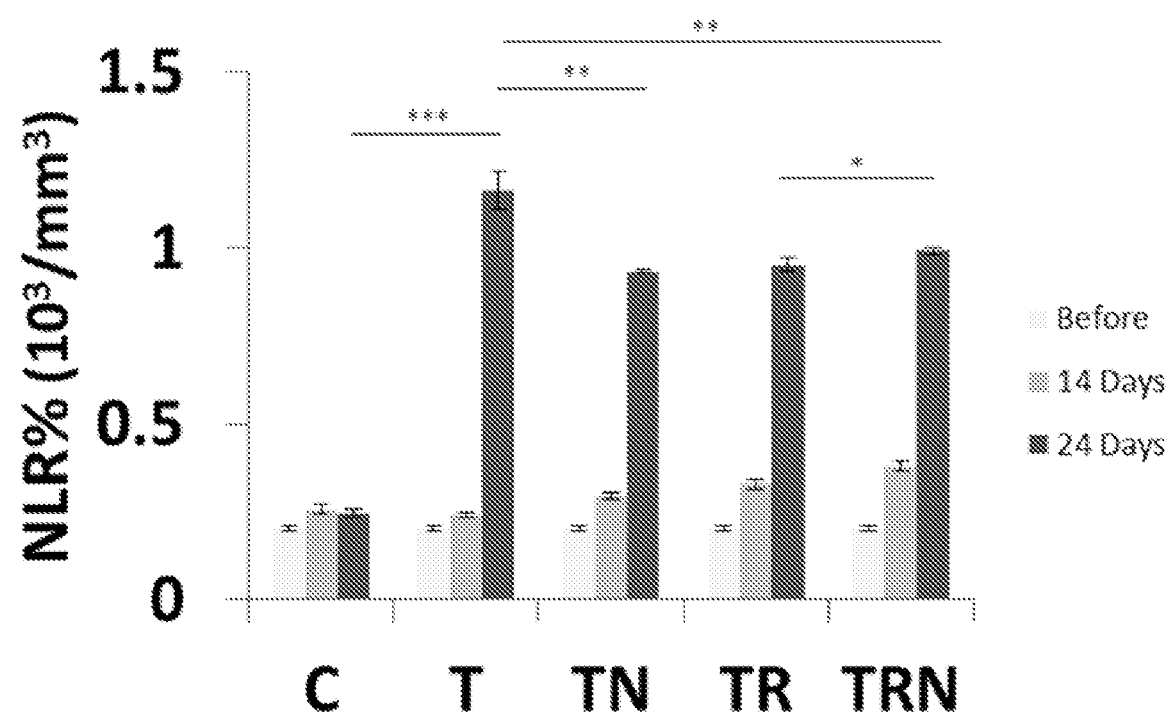
Figure 11A:
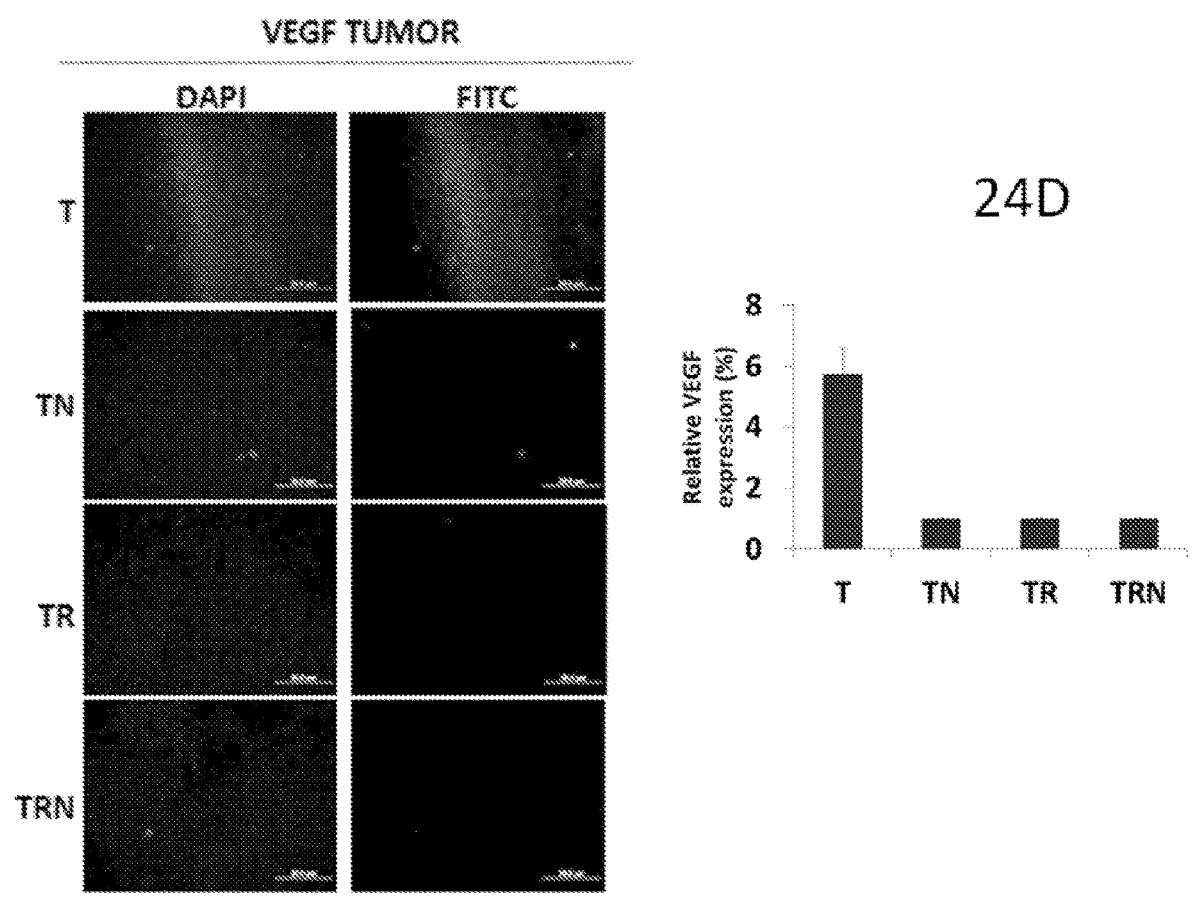
FIGS. 11A to 11D.
Figure 11B:
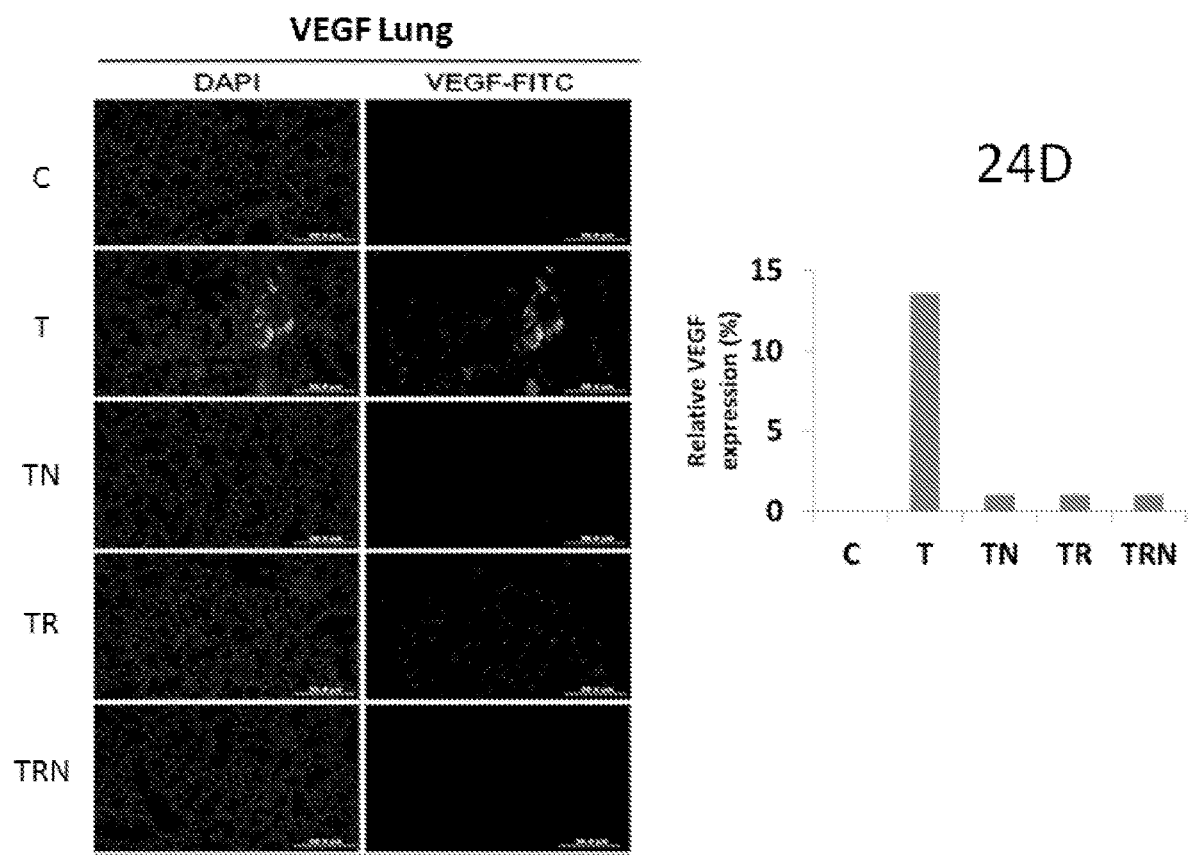
Figure 11C:
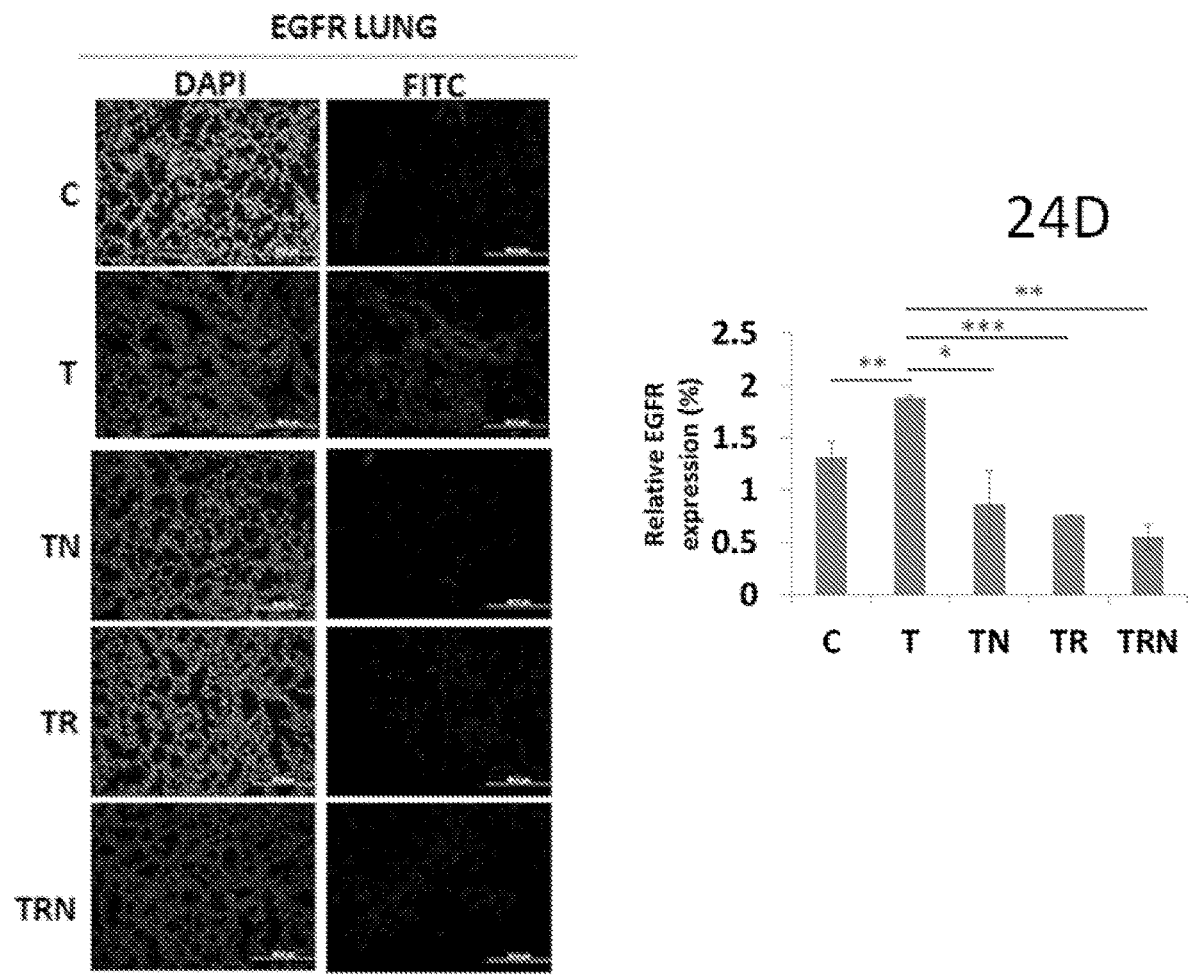
Figure 11D:
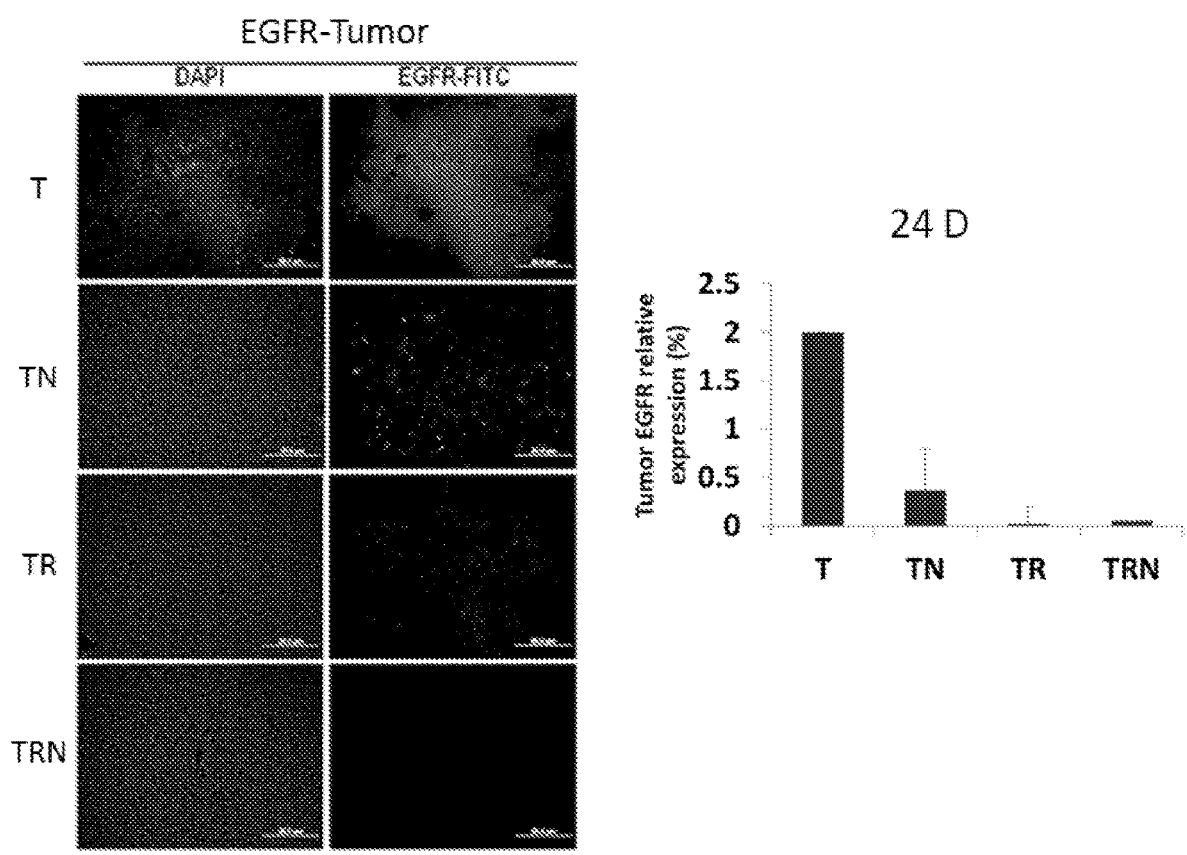

It should be appreciated that repeated rounds of radiotherapy are known to have deleterious effects on subject's nutritional status (at least in part reflected by serum albumin) and to result in suppression of production of various blood cell types. Results from serum albumin and blood cell characterization studies following treatment with nutritional supplement of the inventive concept, radiotherapy, and combined nutritional supplement of the inventive concept and radiotherapy using the protocol shown in FIG. 9 are shown in FIGS. 10A to 10C. As shown, treatment with the nutritional supplement is effective in normalizing these parameters, particularly when the nutritional supplement is provided in combination with radiotherapy.

Surprisingly, treatment with nutritional supplement of the inventive concept, radiotherapy, and combined nutritional supplement of the inventive concept and radiotherapy using the protocol shown in FIG. 9 also has an impact on both expression of tumor cell markers and tumor cell metastasis. In the following studies the tumor cells selected for implantation are derived from a lung tumor and have a strong tendency to metastasize to the lung from the implantation site. FIGS. 11A to 11D show the results of immunocytochemistry studies of different tissues from mice treated with the protocol shown in FIG. 9. Cell surface markers associated with the tumor cells are notably reduced. It is notable that nutritional supplement of the inventive concept alone can reduce or even eliminate metastasis.

Figure 12:
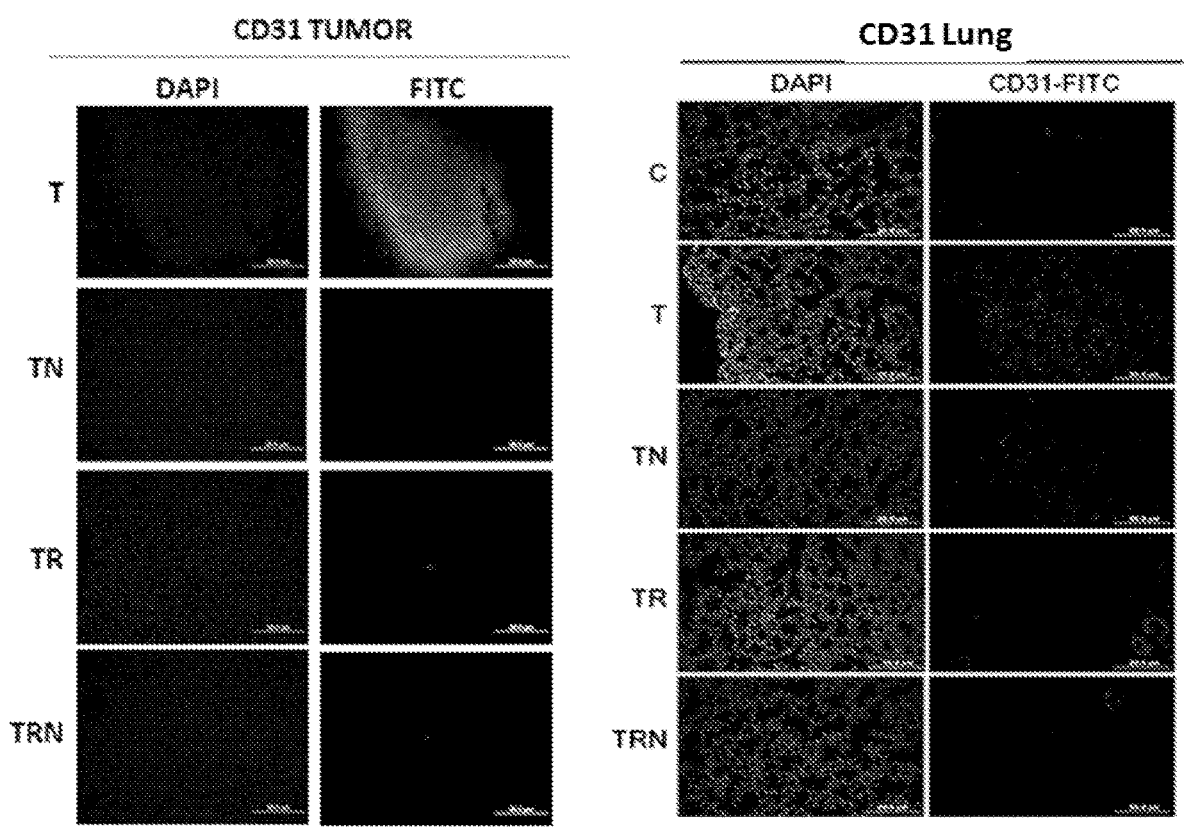
FIG. 12.

Treatment with nutritional supplement of the inventive concept, radiotherapy, and combined nutritional supplement of the inventive concept and radiotherapy using the protocol shown in FIG. 9 also has an impact on tumor stem cells. In the following studies the tumor cells selected for implantation are derived from a lung tumor and have a strong tendency to metastasize to the lung from the implantation site. FIG. 12 shows the results of immunocytochemistry studies of different tissues from mice treated with the protocol shown in FIG. 9. Surprisingly, treatment with nutritional supplement of the inventive concept in the absence of radiotherapy reduces or eliminates the occurrence of cancer stem cells both in the tumor implantation site and at the lung metastatic site, and potentiates the effects of radiotherapy in combined therapy.

Figure 13:
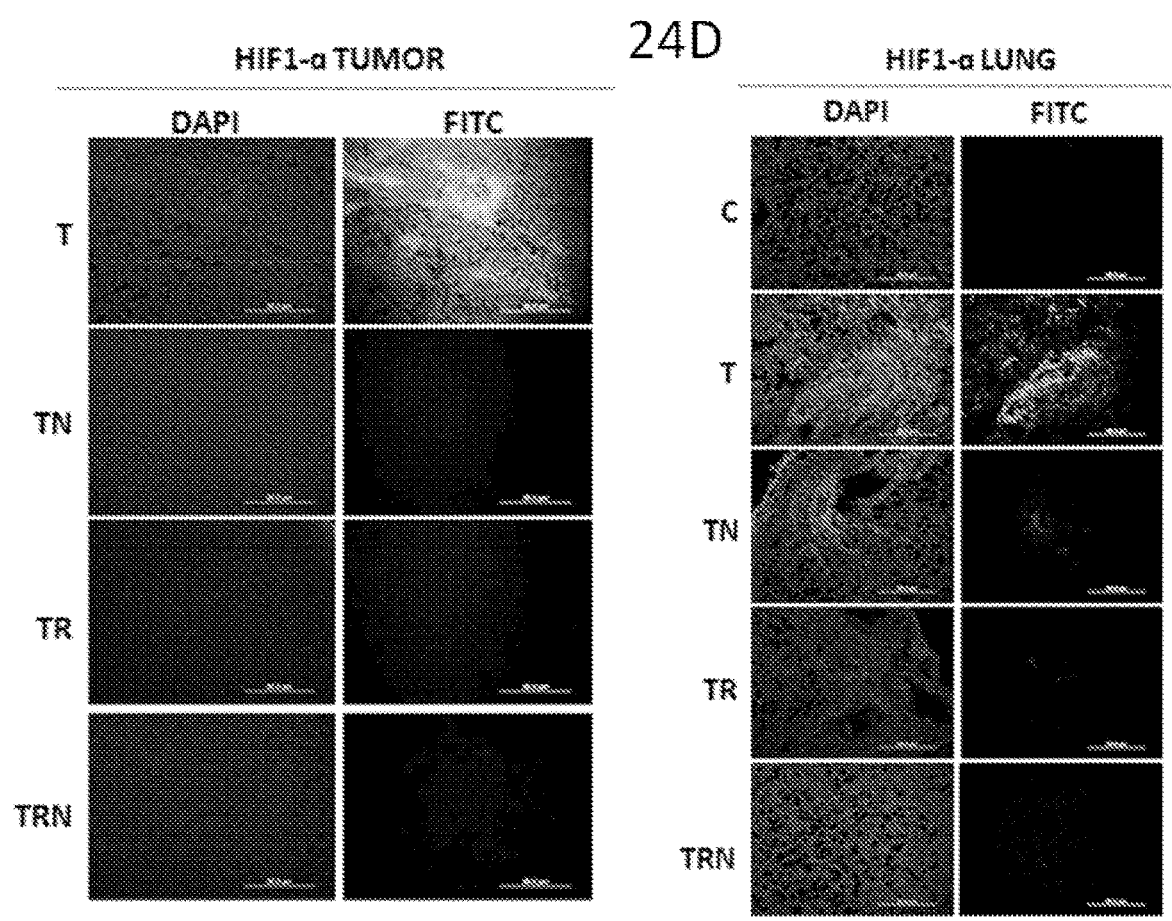
FIG. 13.

Treatment with nutritional supplement of the inventive concept, radiotherapy, and combined nutritional supplement of the inventive concept and radiotherapy using the protocol shown in FIG. 9 also has an impact on hypoxia often found in or among tumor cells. In the following studies the tumor cells selected for implantation are derived from a lung tumor and have a strong tendency to metastasize to the lung from the implantation site. FIG. 13 shows the results of immunocytochemistry studies of different tissues from mice treated with the protocol shown in FIG. 9. Surprisingly, treatment with nutritional supplement of the inventive concept in the absence of radiotherapy reduces or eliminates the occurrence of hypoxia markers in both in the tumor implantation site and at the lung metastatic site, and potentiates the effects of radiotherapy when used in combination.

Treatment with nutritional supplement of the inventive concept, radiotherapy, and combined nutritional supplement of the inventive concept and radiotherapy using the protocol shown in FIG. 9 also has an impact on apoptic activity in tumor cells. Results of qPCR studies for expression of apoptosis markers at 24 days from tumor cell implantation in mice are shown in FIG. 14. Surprisingly, treatment with nutritional supplement of the inventive concept both enhances the effect of radiotherapy and increases expression of apoptosis-related genes in the absence of radiotherapy.

Figure 15:
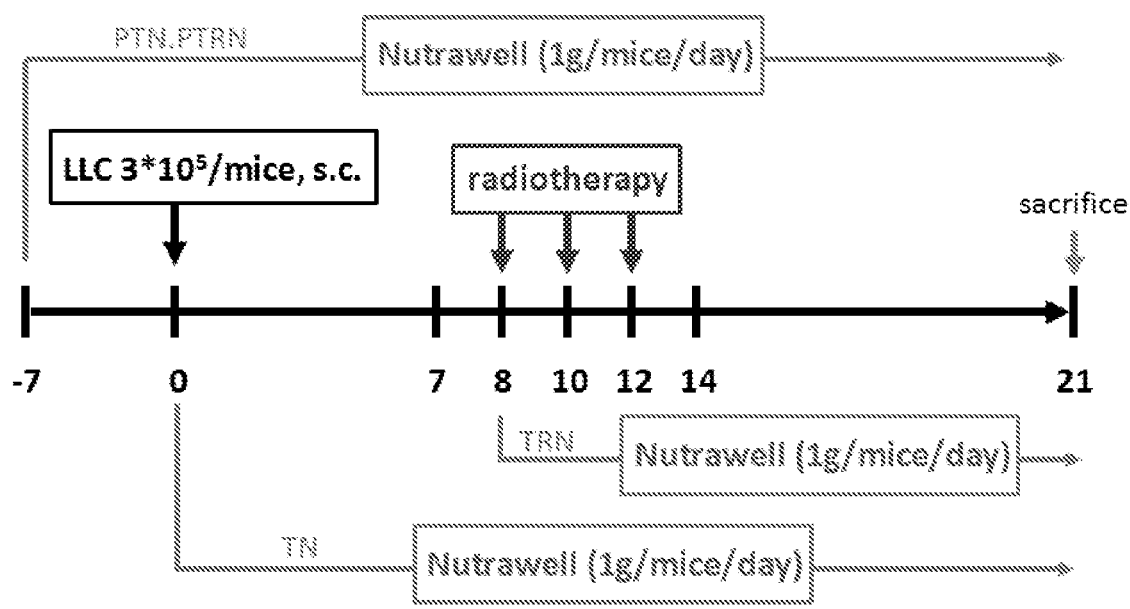
FIG. 15.

Another treatment protocol utilizing multiple rounds of radiotherapy is shown in FIG. 15. Treatment groups resulting from the protocol shown in FIG. 15 are shown in Table 4.

TABLE 4

|   |      |                                       | Sacrifice (14$^{th}$ day) | Sacrifice (24$^{th}$ day) |
|---|------|---------------------------------------|---------------------------|---------------------------|
| 1 | C    | Control                               | N = 6                     | N = 6                     |
| 2 | T    | Tumor                                 | N = 6                     | N = 6                     |
| 3 | TN   | Tumor + Nutrawell                     | N = 6                     | N = 6                     |
| 4 | T3R  | Tumor + Radiotherapy (X3)             | N = 6                     | N = 6                     |
| 5 | T3RN | Tumor + Radiotherapy (X3) + Nutrawell | N = 6                     | N = 6                     |

Figure 16:
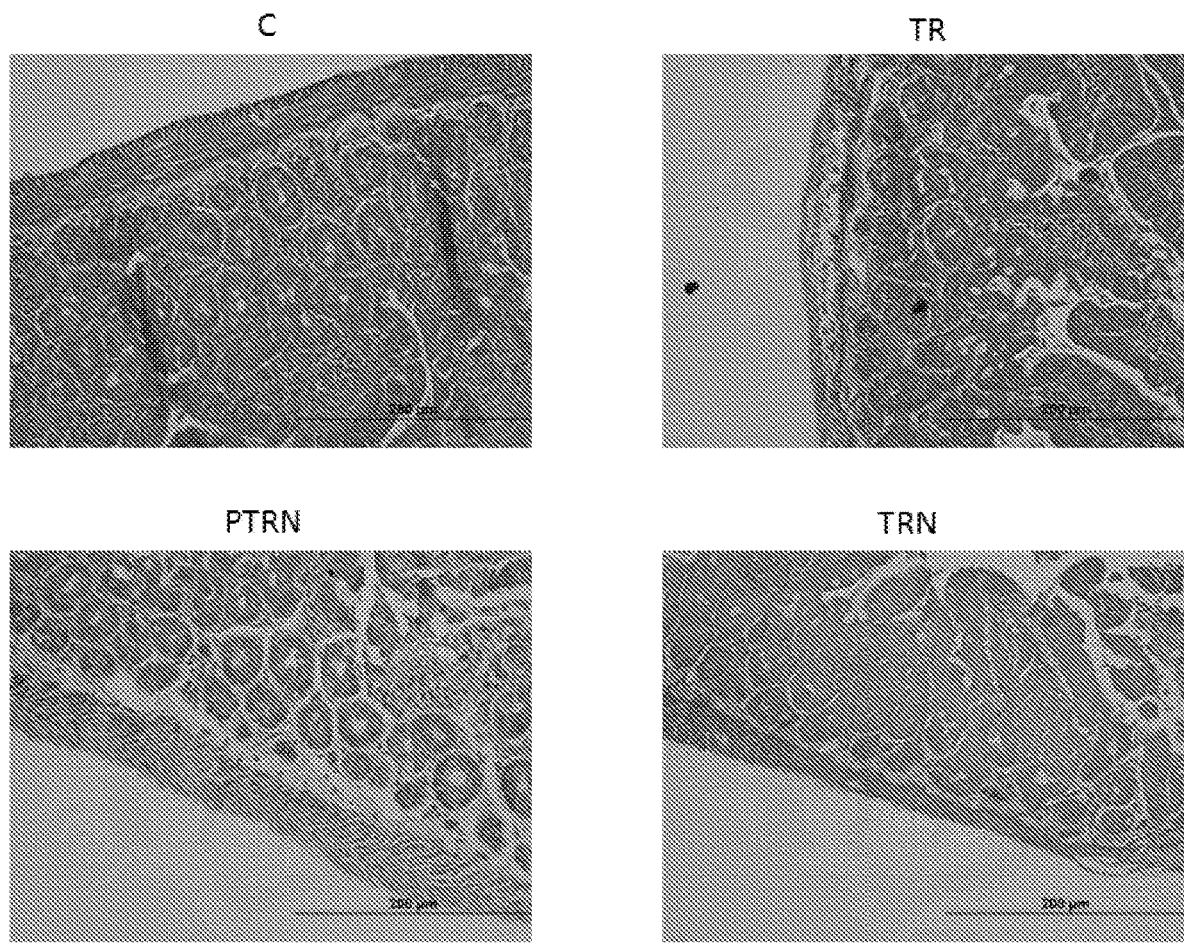
FIG. 16.

In this protocol treatment with the nutritional supplement of the inventive concept was initiated prior to tumor cell implantation, at the time of tumor cell implantation, and at the initiation of radiotherapy. Such a protocol was used to determine the effect of cotherapy with nutritional supplement of the inventive concept and radiotherapy on cellular structures in the gut of tumor-implanted mice. Loss of intestinal absorption and the resulting malnutrition are a well known side effect of radiotherapy, and is thought to be due to the loss of rapidly replicating brush cells in the gut. FIG. 16 shows photomicrographs that demonstrate the effect of supplementation of nutritional supplement of the inventive concept on the cellular architecture of the gut during radiotherapy. As shown, supplementation with NutraWell not only maintains but, surprisingly, can also enhance the intestinal brush border during radiotherapy.

Figure 17A:
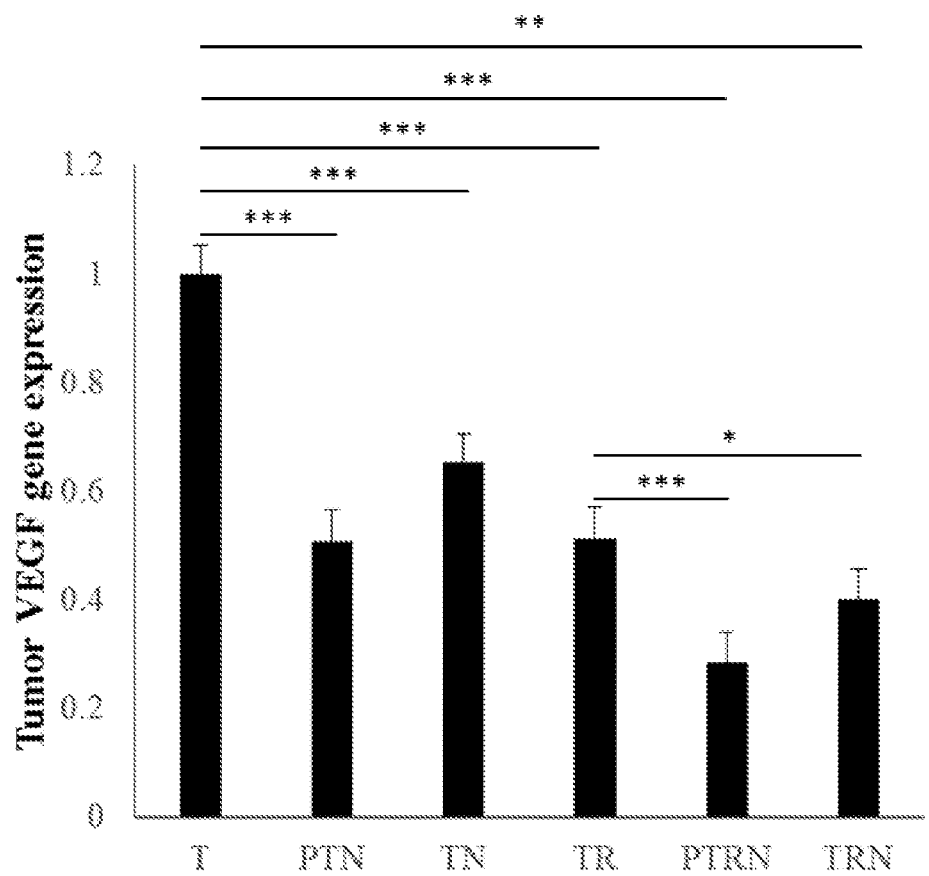
FIGS. 17A to 17F.
Figure 17B:
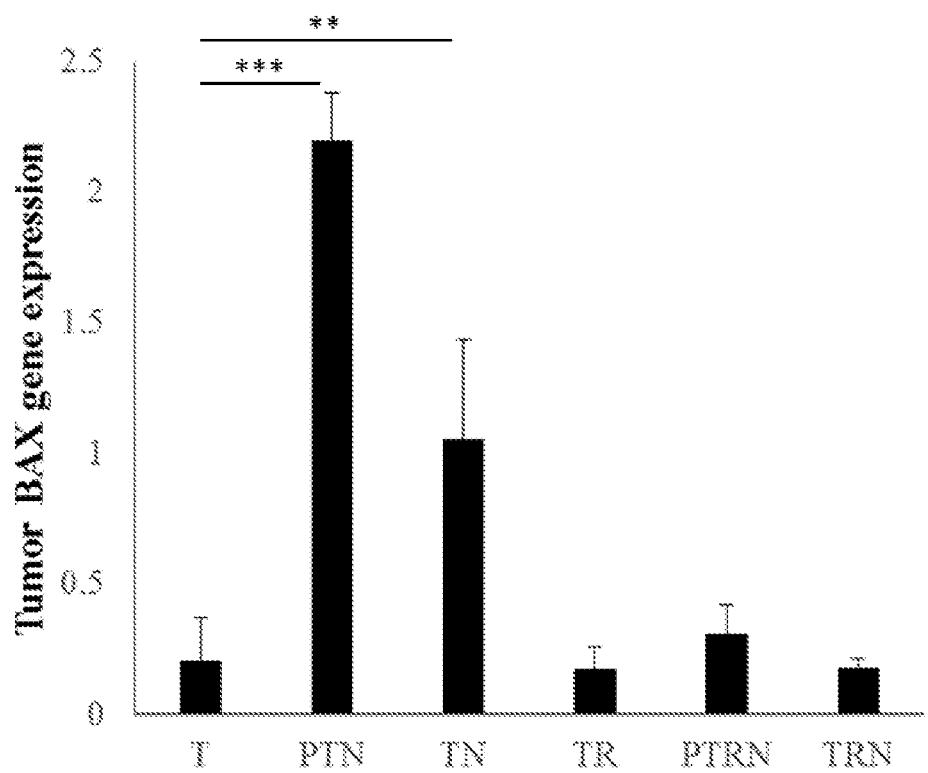
Figure 17C:
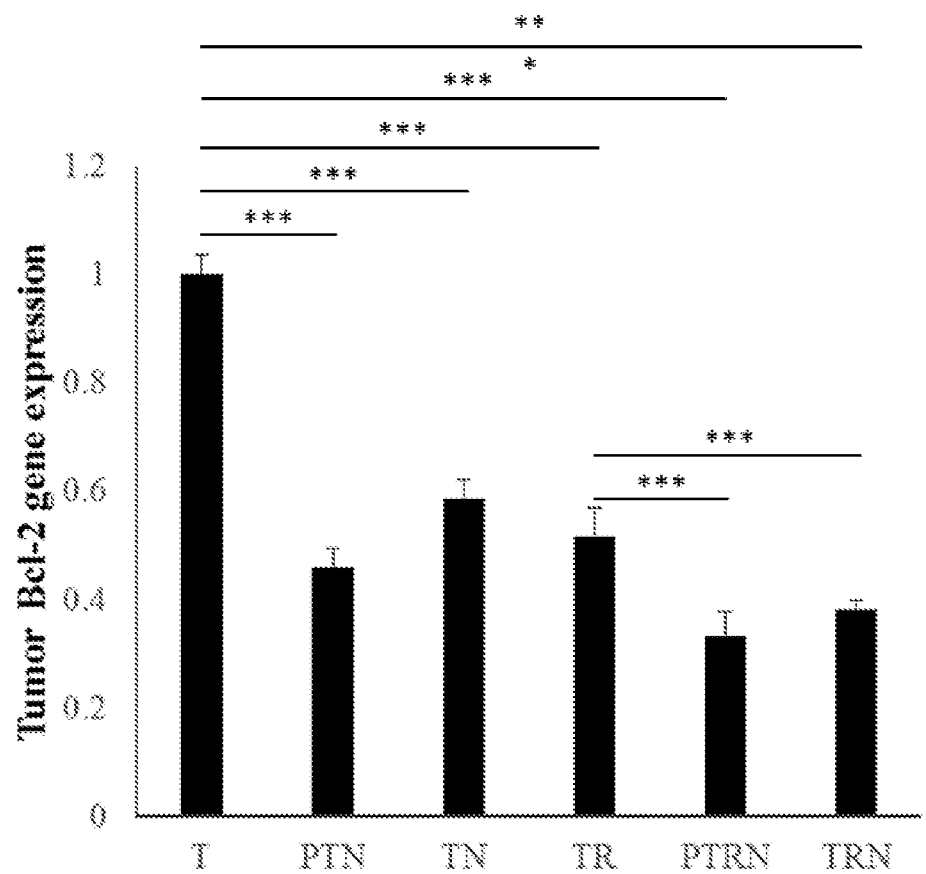
Figure 17D:
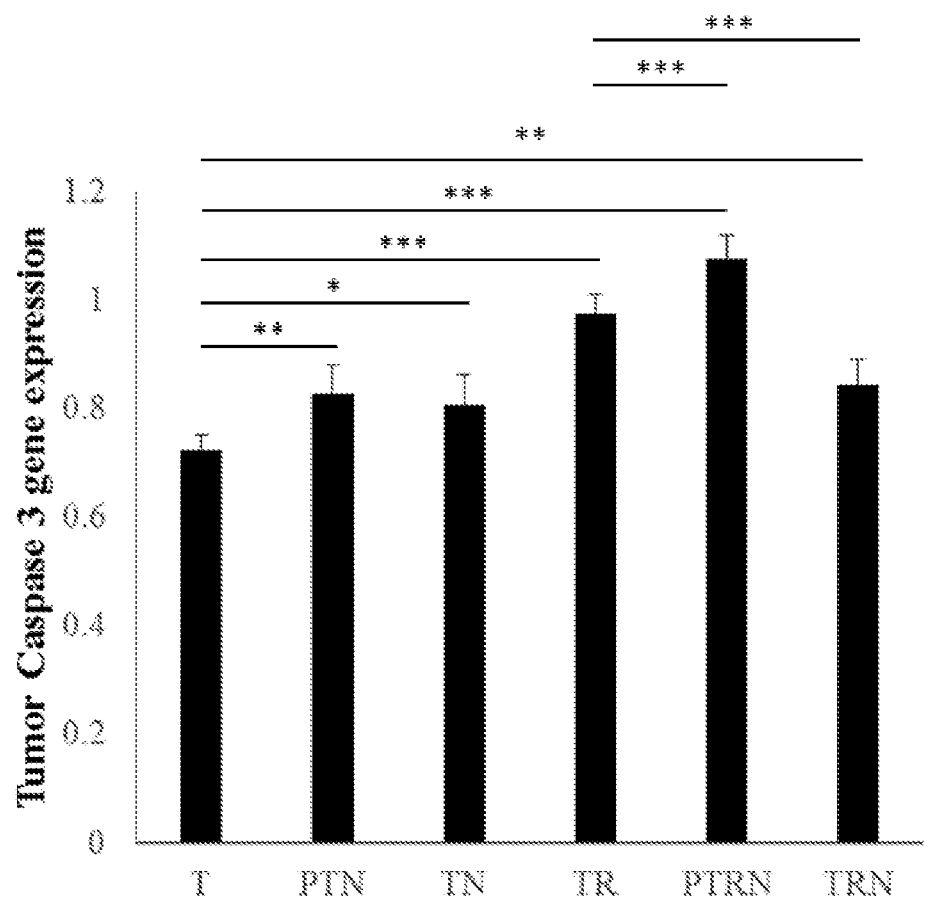
Figure 17E:
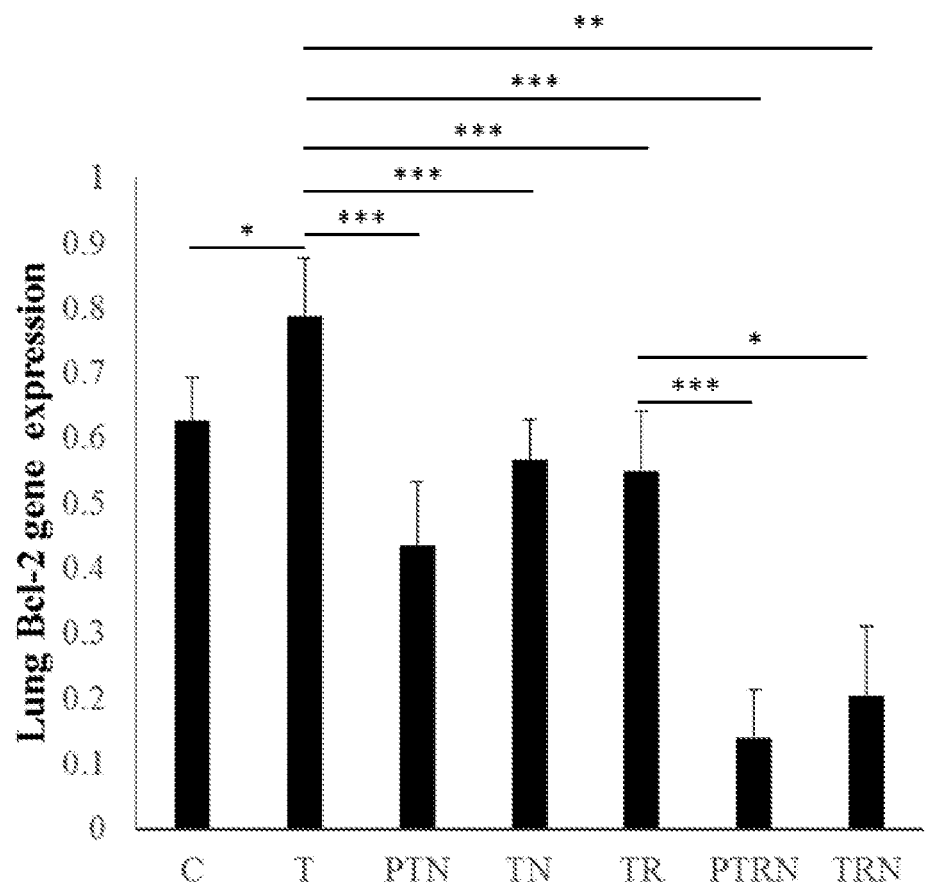
Figure 17F:
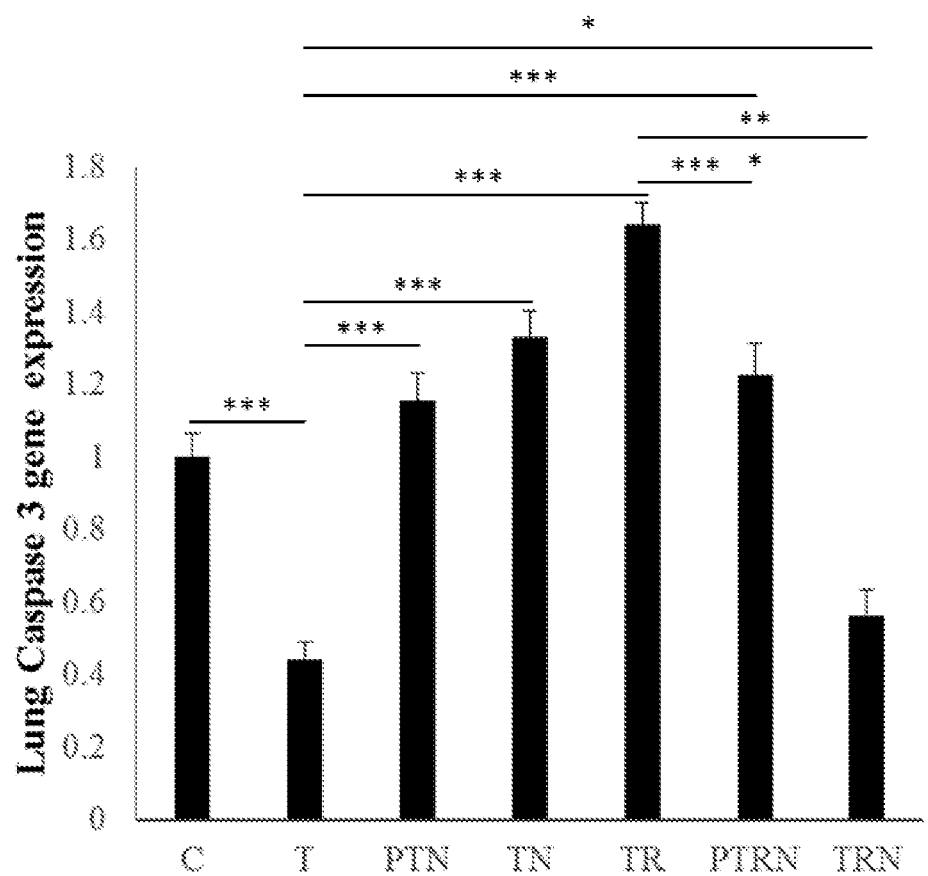

Surprisingly, treatment with nutritional supplement of the inventive concept has been found to modify expression of certain genes in tumor cells and lungs if tumor-implanted mice in vivo, both in enhancing the effects of radiotherapy and when provided without (e.g. prior to) radiotherapy. Results of qPCR studies of gene expression (e.g. angiogenic factor-related, apoptosis-related, etc.) in tumor cells from mice treated by the protocol shown in FIG. 15 are shown in FIGS. 17A to 17F. It should be appreciated that FIGS. 17E and 17F show results from tumor cells that have metastasized from the initial implantation site. As shown, expression of VEGF and Bcl-2 are reduced, while Caspase 3 is elevated. BAX shows a more complex response, being elevated in animals treated with nutritional supplement of the inventive concept and the elevation suppressed when used in combination with radiotherapy.

Figure 18:
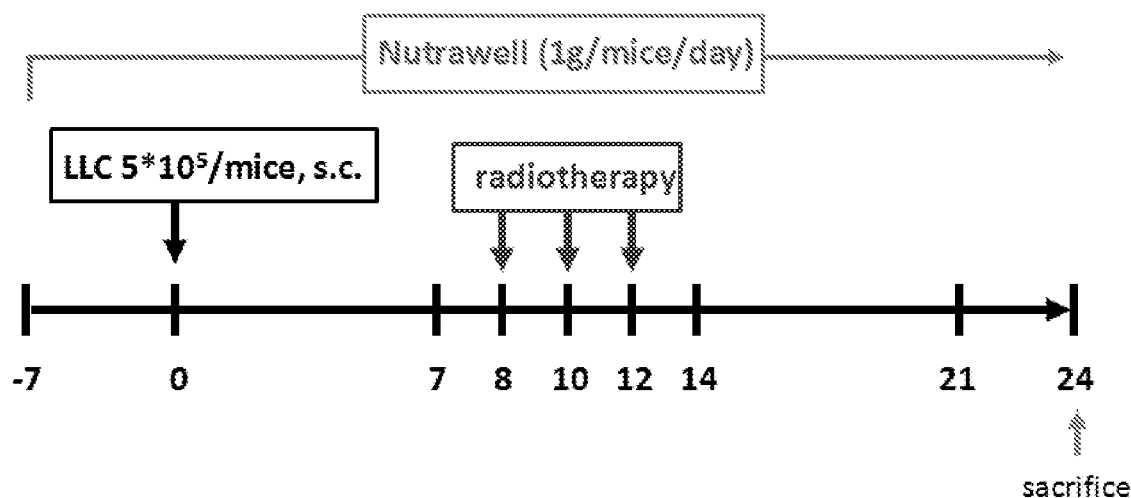
FIG. 18.

Another protocol for utilizing provision of nutritional supplement of the inventive concept with radiotherapy is shown in FIG. 18. A summary of the treatment groups generated by the protocol shown in FIG. 18 is provided in Table 5.

TABLE 5

|   |      |                                       | Sacrifice (24$^{th}$ day) |
|---|------|---------------------------------------|---------------------------|
| 1 | C    | Control                               | N = 6                     |
| 2 | T    | Tumor                                 | N = 6                     |
| 3 | TN   | Tumor + Nutrawell                     | N = 6                     |
| 4 | T3R  | Tumor + Radiotherapy (X3)             | N = 6                     |
| 5 | T3RN | Tumor + Radiotherapy (X3) + Nutrawell | N = 6                     |

Figure 19A:
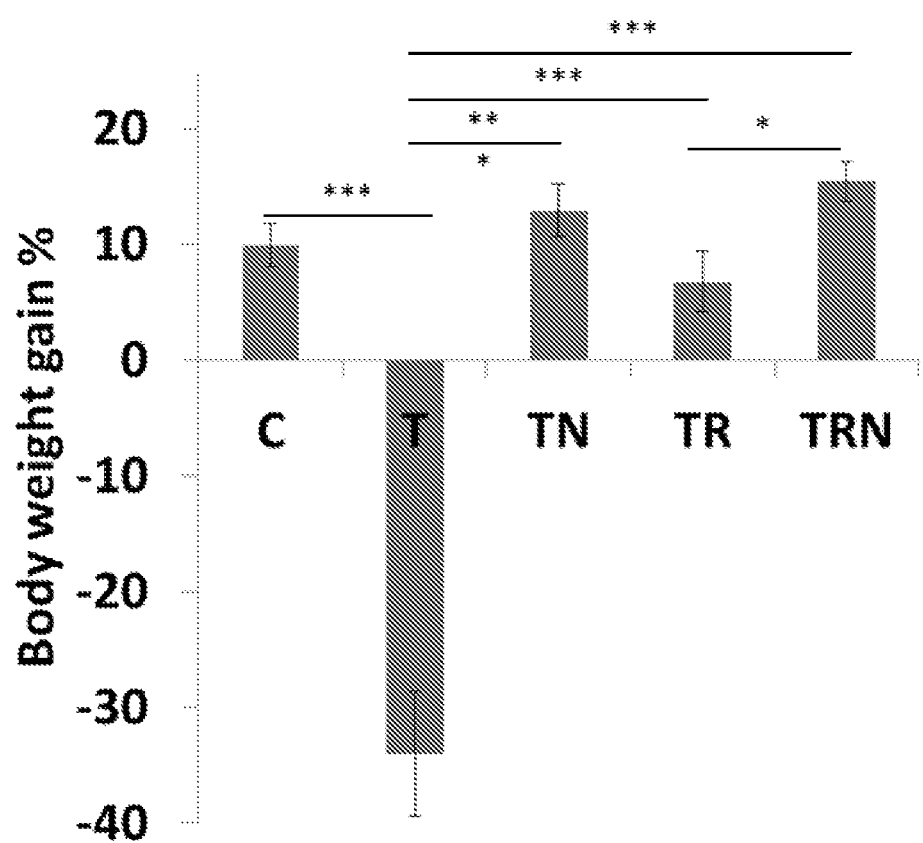
FIGS. 19A and 19B.
Figure 19B:
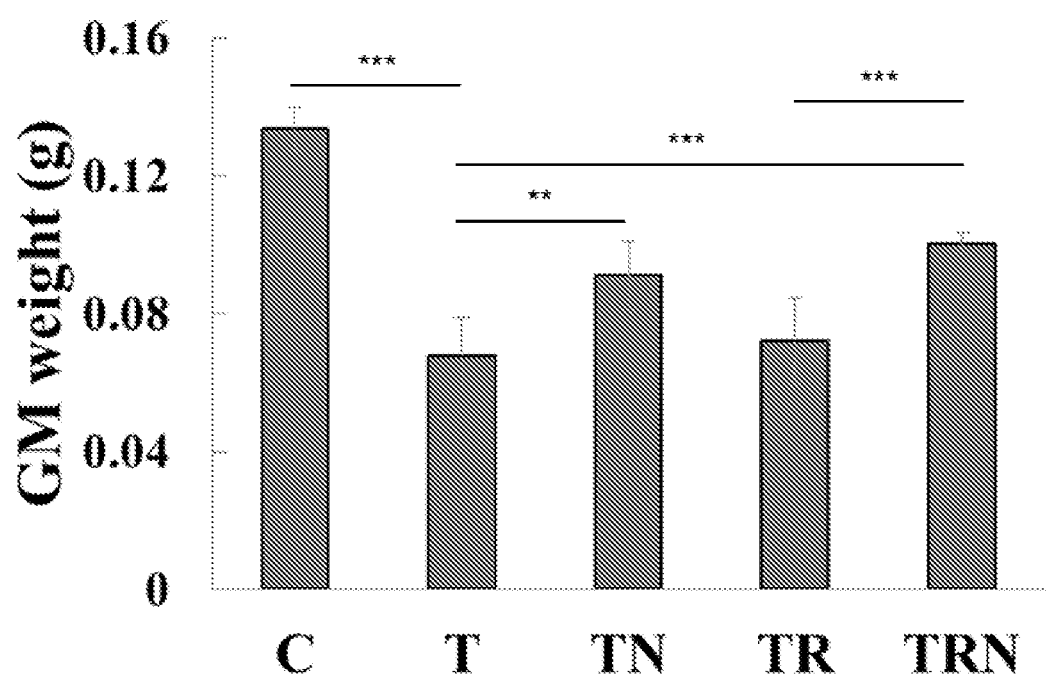

In this protocol nutritional supplement of the inventive concept is provided 7 days prior to implantation of tumor cells, with radiotherapy taking place on days 8, 10, and 12 following implantation. Mice were sacrificed on day 24 following implantation. Such a protocol was used to evaluate the effects of the nutritional supplement on a highly characteristic side effect of radiotherapy-weight loss. The effect of nutritional supplement of the inventive concept on loss of body mass and in particular muscle mass following repeated radiotherapy is shown in FIGS. 19A and 19B. It should be appreciated that body mass was characterized following removal of the tumor mass. It is apparent that pre-treatment with nutritional supplement of the inventive concept effectively prevents the loss of body mass (relative to control subjects) resulting from repeated radiotherapy.

Figure 20:
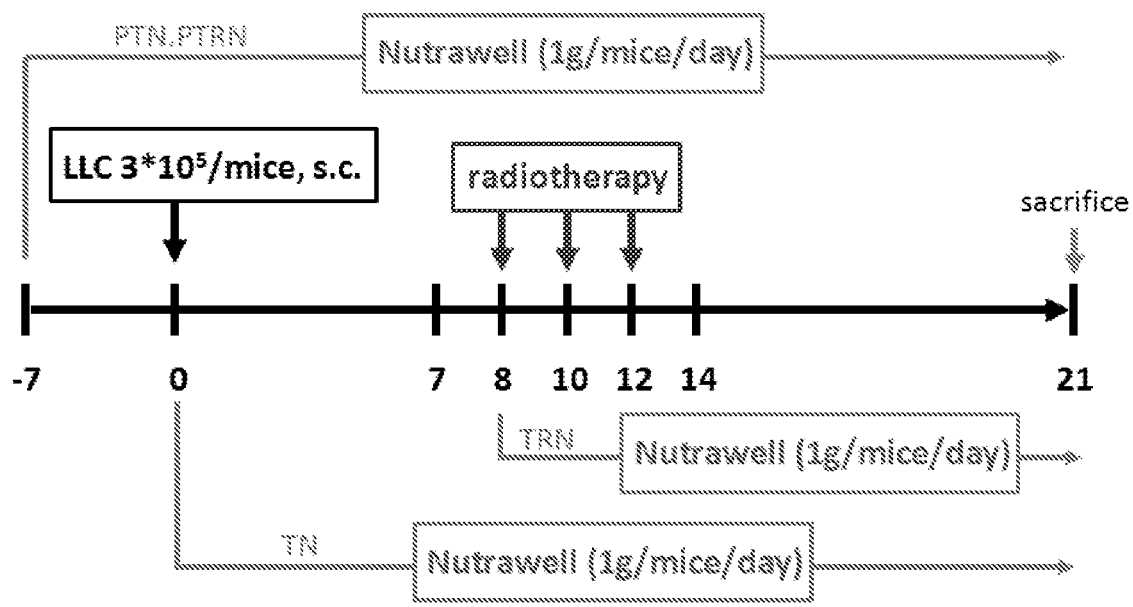
FIG. 20.

Another treatment protocol is shown in FIG. 20. A summary of the treatment groups generated by the protocol shown in FIG. 20 is provided in Table 6.

TABLE 6

|   |     |                                  | Sacrifice (21$^{st}$ day) |
|---|-----|----------------------------------|---------------------------|
| 1 | C   | Control                          | N = 6                     |
| 2 | T   | Tumor                            | N = 6                     |
| 3 | PTN | Tumor + Nutrawell (−7 day start) | N = 6                     |
| 4 | TN  | Tumor + NutraWell (0 day start)  | N = 6                     |
| 5 | TR  | Tumor + Radiotherapy (3 Gy X 3)  | N = 6                     |

TABLE 6-continued

| | | | Sacrifice (21st day) |
|---|---|---|---|
| 6 | PTRN | Tumor + Radiotherapy (3 Gy X 3) + Nutrawell (−7 day start) | N = 6 |
| 7 | TRN | Tumor + Radiotherapy (3 Gy X 3) + Nutrawell (8 day start) | N = 6 |

Figure 21:
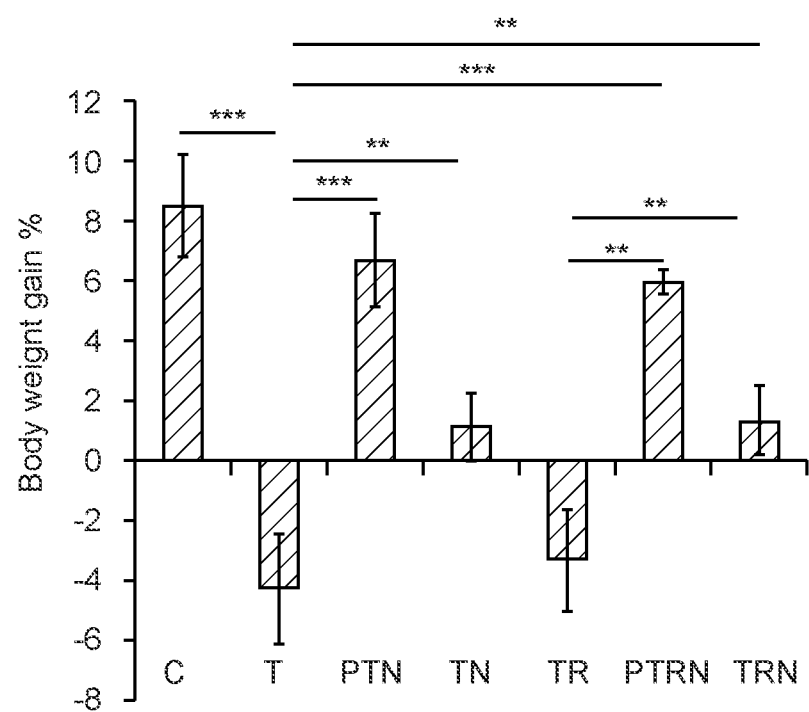
FIG. 21.

In this protocol radiotherapy is provided on days 8, 10, and 12 following implantation of tumor cells. Nutritional supplement of the inventive concept is provided either 7 days prior to implantation, the day of implantation, or on the first radiotherapy. Mice are sacrificed on day 21 following tumor cell implantation. This protocol was also used to evaluate the effectiveness of the nutritional supplement on treating radiotherapy-related weight loss. The effect of nutritional supplement of the inventive concept on loss of body mass and muscle mass when provided prior to and provided coincident with the initiation of repeated radiotherapy is shown in FIG. 21. It should be appreciated that body mass was characterized following removal of the tumor mass. It is apparent that pre-treatment with nutritional supplement of the inventive concept effectively reverses the loss of body mass (relative to control subjects) resulting from repeated radiotherapy.

Figure 22:
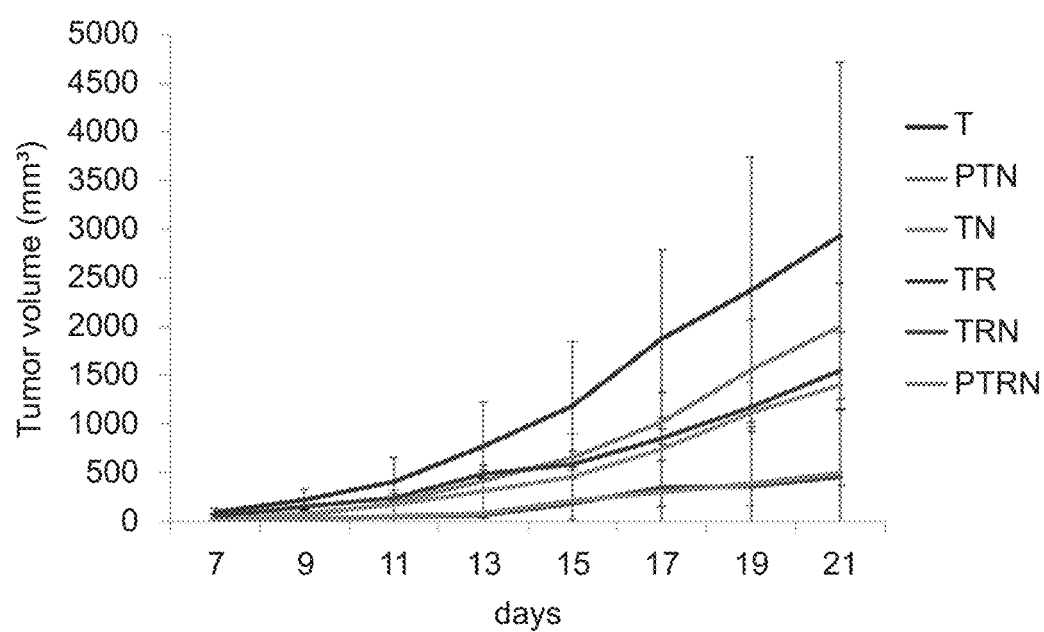
FIG. 22.

Inventors have also found that pre-treatment with nutritional supplement of the inventive concept enhances the reduction in tumor volume seen on repeated radiotherapy. Results of measurements of tumor volume during treatment of mice with the protocol shown in FIG. 20 are shown in FIG. 22. As shown, treatment with the nutritional supplement is effective in reducing the increase in tumor volume over time, particularly in combination with radiotherapy.

Figure 23A:
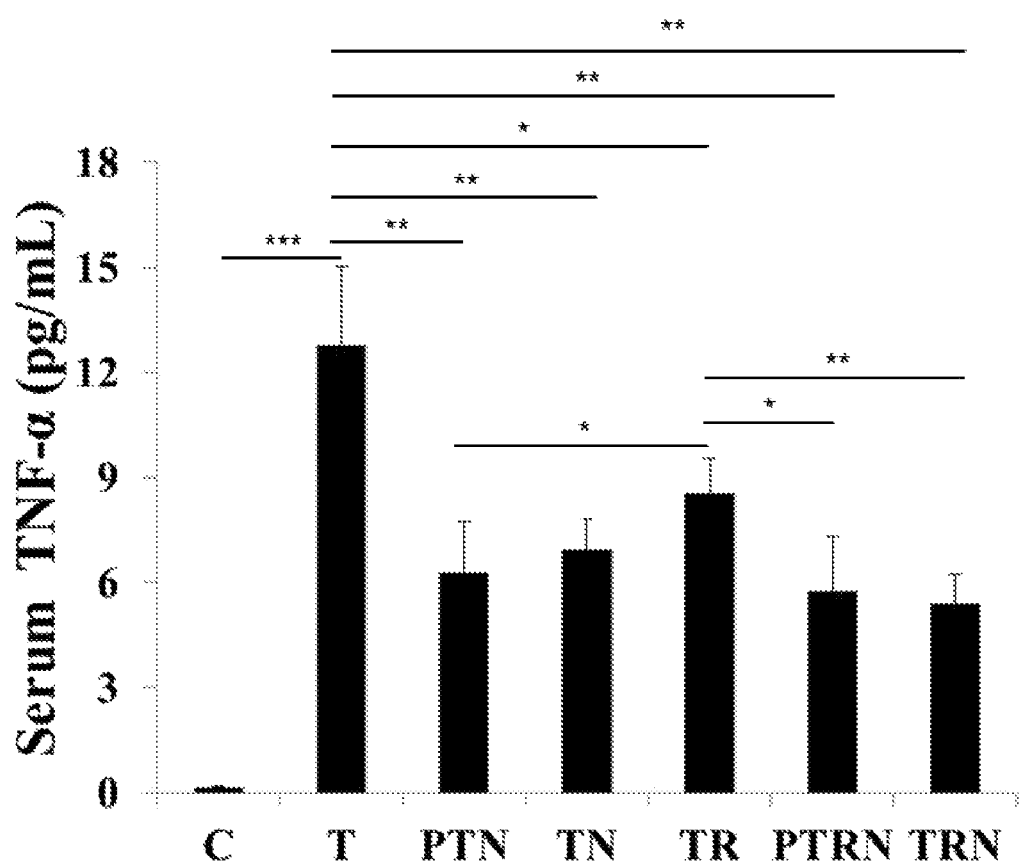
FIGS. 23A and 23B.
Figure 23B:
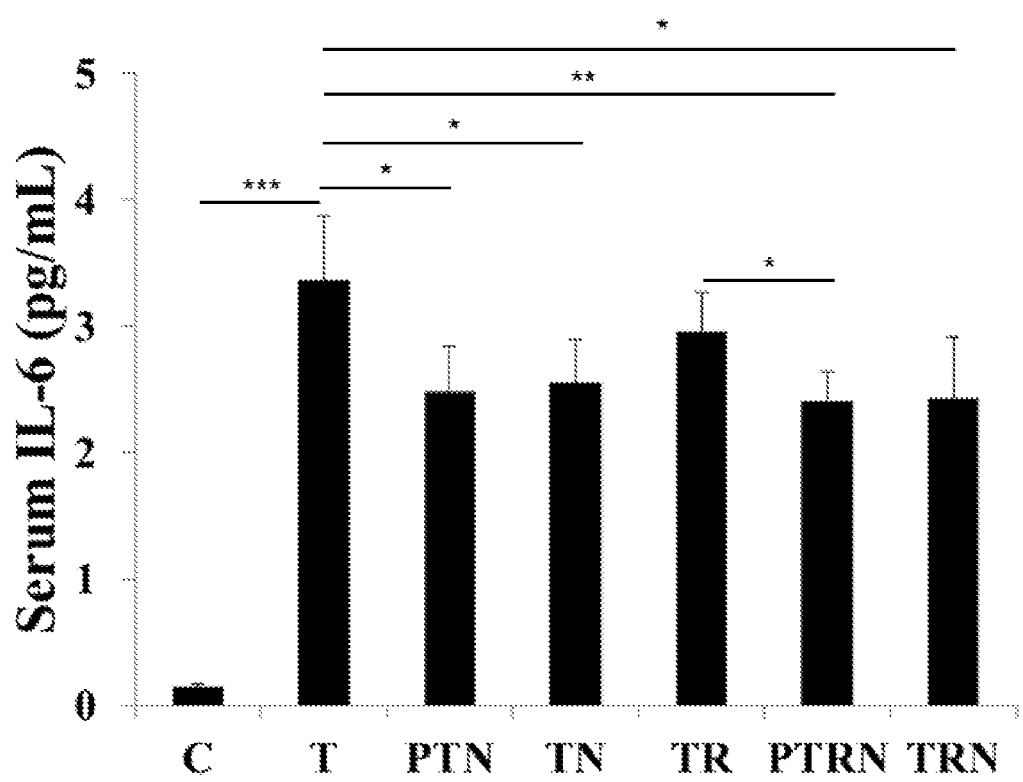

The presence of tumors can also result in inflammation, which can be characterized by the presence of pro-inflammatory cytokines in serum. FIGS. 23A and 23B show the effect of administration of nutritional supplement of the inventive concept with repeated radiotherapy on the concentration of pro-inflammatory cytokines in mice treated as in the protocol shown in FIG. 20. As shown, treatment with the nutritional supplement is effective in reducing the amount of pro-inflammatory cytokines found in serum of tumor-bearing animals, particularly in combination with radiotherapy.

While nutritional supplements of the inventive concept have been shown to be effective in enhancing the effects of radiotherapy and/or reducing the side effects of radiotherapy, Inventors contemplate that similar benefits are found when such nutritional supplements are used in combination with immunotherapies-particularly immunotherapies directed towards the treatment of cancer. Such immunotherapy in combination with use of a nutritional supplement of the inventive concept can be used in combination (e.g. either simultaneously or sequentially) with a radiotherapy.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a tumor, comprising:
applying a radiotherapy protocol to a patient in need of treatment; and
providing the patient with a nutritional supplement comprising a functional nutritional supplement, wherein the functional nutritional supplement comprises Maltodextrin, Whey Protein Isolate, Whey Protein Concentrate, Fructooligosaccharides/Inulin, Oat Fiber, Soy Protein, Lecithin, Milk:Non-fat, Rice Protein Powder, Calcium Caseinate, Flax Seed Oil, Canola Oil, Borage Oil, Olive Oil, Fish Oil, Lemon Oil, Orange Oil, Mixed Tocopherols, Potassium Phosphate, Calcium Carbonate, Choline Bitartrate, Sodium Chloride, Calcium Phosphate, Ascorbic Acid, Potassium Chloride, Magnesium Oxide, Selenium as a complex with a peptide or amino acid as a result of metabolism of selenium by Yeast, Chromium as a complex with a peptide or amino acid as a result of metabolism of chromium by Yeast, Molybdenum as a complex with a peptide or amino acid as a result of metabolism of molybdenum by Yeast, Inositol, Zinc Sulfate, Vitamin E, Niacinamide, Ferric Orthophosphate, Calcium Pantothenate, Manganese Sulfate, Beta Carotene, Copper Gluconate, Vitamin D3, Vitamin K2, Pyridoxine, Potassium Iodide, Riboflavin, Thiamine, Vitamin K1, Vitamin A, Folic Acid, d-Biotin, Vitamin B12, L-Carnitine, L-Glutamine, L-Arginine, Taurine, L-Lysine, Alpha Lipoic Acid, Resveratrol, Co-Enzyme Q10, Glycine, Proline, Lact *Acidophilus* culture, Bifido Bifidium culture, Lac *Bulgaricus* culture, Bifido *Longum* culture, Strep *Thermophilus* culture, Papain, Pepsin, Lipase, Bromelain, Pancreatin, Lactase, Betaine, Pineapple Juice Powder, *Papaya* Fruit Powder, Quercetin, EGCG, OPC, Anthocyanins, Ellagic Acid, Astaxanthin, dried or lyophilized fruiting bodies of *Cordyceps*, dried or lyophilized fruiting bodies of *Ganoderma Lucidum*, dried or lyophilized fruiting bodies of Shiitake, dried or lyophilized fruiting bodies of Maitake, and dried or lyophilized fruiting bodies of Turkey Tail,
wherein the functional nutritional supplement is provided in an amount to provide a synergistic effect in regard to reducing tumor volume or weight when provided in combination with the radiotherapy protocol.

2. The method of claim 1, wherein the nutritional supplement is provided to the patient prior to the initiation of radiotherapy.

3. The method of claim 1, wherein the nutritional supplement is provided to the patient concurrent with radiotherapy.

4. The method of claim 1, wherein the nutritional supplement further comprises one or more flavorants selected from the group consisting of Brown Sugar, Honey, French Vanilla Flavor, and Vanilla Masking Flavor.

5. A method of modulating a disease-associated activity in a tumor, comprising:
providing a nutritional supplement to a tumor or an animal having a tumor, wherein the nutritional supplement comprises a functional nutritional supplement comprising Maltodextrin, Whey Protein Isolate, Whey Protein Concentrate, Fructooligosaccharides/Inulin, Oat Fiber, Soy Protein, Lecithin, Milk:Non-fat, Rice Protein Powder, Calcium Caseinate, Flax Seed Oil, Canola Oil, Borage Oil, Olive Oil, Fish Oil, Lemon Oil, Orange Oil, Mixed Tocopherols, Potassium Phosphate, Calcium Carbonate, Choline Bitartrate, Sodium Chloride, Calcium Phosphate, Ascorbic Acid, Potassium Chloride, Magnesium Oxide, Selenium as a complex with a peptide or amino acid as a result of metabolism of selenium by Yeast, Chromium as a complex with a peptide or amino acid as a result of metabolism of chromium by Yeast, Molybdenum as a complex with a peptide or amino acid as a result of metabolism of molybdenum by Yeast, Inositol, Zinc Sulfate, Vitamin E, Niacinamide, Ferric Orthophosphate, Calcium Pantothenate, Manganese Sulfate, Beta Carotene, Copper Gluconate, Vitamin D3, Vitamin K2, Pyridoxine, Potassium Iodide, Riboflavin, Thiamine, Vitamin K1, Vitamin A, Folic Acid, d-Biotin, Vitamin B12, L-Carnitine, L-Glutamine, L-Arginine, Taurine, L-Lysine, Alpha Lipoic Acid, Resveratrol, Co-Enzyme Q10, Glycine, Proline, Lact *Acidophilus* culture, Bifido Bifidium culture, Lac *Bulgaricus* culture, Bifido *Longum* culture, Strep *Thermophilus* culture, Papain, Pepsin, Lipase, Bromelain, Pancreatin, Lactase, Betaine, Pineapple Juice Powder, *Papaya* Fruit Powder, Quercetin, EGCG, OPC, Anthocyanins, Ellagic Acid, Astaxanthin, dried or lyophilized fruiting bodies of *Cordyceps*, dried or lyophilized fruiting bodies of *Ganoderma Lucidum*, dried or lyophilized fruiting bodies of Shiitake, dried or lyophilized fruiting bodies of Maitake, and dried or lyophilized fruiting bodies of Turkey Tail,
wherein the nutritional supplement is provided in an amount to modulate the disease-associated activity of the tumor, wherein the disease associated activity is selected from the group consisting of expression of a gene of the tumor, metastasis from the tumor, angiogenesis, and growth of a cancer stem cell.

6. The method of claim 5, wherein the nutritional supplement is provided to a patient prior to the initiation of radiotherapy.

7. The method of claim 5, wherein the nutritional supplement is provided to a patient concurrent with radiotherapy.

8. The method of claim 5, wherein the nutritional supplement further comprises one or more flavorants selected from the group consisting of Brown Sugar, Honey, French Vanilla Flavor, and Vanilla Masking Flavor.

9. The method of claim 5, wherein the gene encodes for an angiogenesis factor.

10. The method of claim 5, wherein the gene encodes for an apoptosis factor.

11. The method of claim 5, wherein the disease associated activity is metastasis from the tumor, and wherein modulation comprises a reduction in metastatic activity.

12. The method of claim 5, wherein the disease associated activity is angiogenesis, and wherein modulation comprises reducing angiogenic activity in the tumor.

13. The method of claim 5, wherein the disease associated activity is growth of a cancer stem cell, and wherein modulation comprises reducing growth of a cancer stem cell of the tumor.

14. A nutritional supplement essentially consisting of Maltodextrin, Whey Protein Isolate, Whey Protein Concentrate, Fructooligosaccharides/Inulin, Oat Fiber, Soy Protein, Lecithin, Milk:Non-fat, Rice Protein Powder, Calcium Caseinate, Flax Seed Oil, Canola Oil, Borage Oil, Olive Oil, Fish Oil, Lemon Oil, Orange Oil, Mixed Tocopherols, Potassium Phosphate, Calcium Carbonate, Choline Bitartrate, Sodium Chloride, Calcium Phosphate, Ascorbic Acid, Potassium Chloride, Magnesium Oxide, Selenium as a complex with a peptide or amino acid as a result of metabolism of selenium by Yeast, Chromium as a complex with a peptide or amino acid as a result of metabolism of chromium by Yeast, Molybdenum as a complex with a peptide or amino acid as a result of metabolism of molybdenum by Yeast, Inositol, Zinc Sulfate, Vitamin E, Niacinamide, Ferric Orthophosphate, Calcium Pantothenate, Manganese Sulfate, Beta Carotene, Copper Gluconate, Vitamin D3, Vitamin K2, Pyridoxine, Potassium Iodide, Riboflavin, Thiamine, Vitamin K1, Vitamin A, Folic Acid, d-Biotin, Vitamin B12, L-Carnitine, L-Glutamine, L-Arginine, Taurine, L-Lysine, Alpha Lipoic Acid, Resveratrol, Co-Enzyme Q10, Glycine, Proline, Lact *Acidophilus* culture, Bifido Bifidium culture, Lac *Bulgaricus* culture, Bifido *Longum* culture, Strep *Thermophilus* culture, Papain, Pepsin, Lipase, Bromelain, Pancreatin, Lactase, Betaine, Pineapple Juice Powder, *Papaya* Fruit Powder, Quercetin, EGCG, OPC, Anthocyanins, Ellagic Acid, Astaxanthin, dried or lyophilized fruiting bodies of *Cordyceps*, dried or lyophilized fruiting bodies of *Ganoderma Lucidum*, dried or lyophilized fruiting bodies of Shiitake, dried or lyophilized fruiting bodies of Maitake, and dried or lyophilized fruiting bodies of Turkey Tail.

15. The nutritional supplement of claim 14, further comprising one or more flavorants.

16. The nutritional supplement of claim 14, wherein at least one of the one or more flavorants is selected from the group consisting of Brown Sugar, Honey, French Vanilla Flavor, and Vanilla Masking Flavor.

* * * * *